(12) United States Patent
Marth et al.

(10) Patent No.: US 7,674,577 B2
(45) Date of Patent: Mar. 9, 2010

(54) DIAGNOSIS OF HUMAN GLYCOSYLATION DISORDERS

(75) Inventors: Jamey D. Marth, San Diego, CA (US); Hudson H. Freeze, San Diego, CA (US)

(73) Assignees: The Regents of the University of California, Oakland, CA (US); The Burnham Institute, La Jolla, CA (US)

( * ) Notice: Subject to any disclaimer, the term of this patent is extended or adjusted under 35 U.S.C. 154(b) by 238 days.

(21) Appl. No.: 11/381,941

(22) Filed: May 5, 2006

(65) Prior Publication Data

US 2006/0228762 A1  Oct. 12, 2006

Related U.S. Application Data

(63) Continuation of application No. 09/857,233, filed as application No. PCT/US99/28591 on Dec. 1, 1999, now Pat. No. 7,273,711.

(60) Provisional application No. 60/110,671, filed on Dec. 2, 1998, provisional application No. 60/113,680, filed on Dec. 21, 1998, provisional application No. 60/114,174, filed on Dec. 30, 1998.

(51) Int. Cl.
*G01N 33/53* (2006.01)
*G01N 33/566* (2006.01)
*G01N 33/68* (2006.01)

(52) U.S. Cl. .................. 435/4; 435/7.21; 436/501; 436/63; 436/87; 436/94; 436/827

(58) Field of Classification Search ............ None
See application file for complete search history.

(56) References Cited

U.S. PATENT DOCUMENTS 5,432,059 A * 7/1995 Bean et al. ............... 435/15

OTHER PUBLICATIONS

Hood et al, Immunology, Second Edition, The Benjamin/Cummings Publishing Comapany, Inc., 1984, pp. 24-25.*

Bergmann, Markus et al.; Abnormal surface expression of sialoglycans on B lymphocyte cell lines from patients with carbohydrate deficient glycoprotein syndrome I A (CDGS I A); *Glycobiology*; 1998, pp. 963-972; vol. 8, No. 10.

Chui, Daniel at al.; "Alpha-Mannosidase-II Deficiency Results in Dyserythropoiesis and Unveils an Alternate Pathway in Oligosaccharide Biosynthesis"; *Cell*; 1997; pp. 157-167; vol. 90.

Ellies, Lesley G. et al.; "Core 2 Oligosaccharide Biosynthesis Distinguishes Between Selectin Ligands Essential for Leukocyte Homing and Inflammation"; *Immunity*; 1998; pp. 881-890; vol. 9.

Hennet, Thierry et al.; "Immune Regulation by the ST6Gal Sialyltransferase"; *Proc. Natl. Acad. Sci. U.S.A.*; 1998; pp. 4504-4509; vol. 95.

Metzler, Martina et al.; "Complex Asparagine-linked Oligosaccharides are Required for Morphogenic Events During Post-implantation Development"; *The EMBO Journal*; 1994; pp. 2056-2065; vol. 13.

Priatel, John J. et al.; "Isolation, Characterization and Interaction of the Mouse *Mgat31* Gene: the Bisecting N-acetylglucosamine in Asparagine-linked Oligosaccharides Appears Dispensable for Viability and Reproduction"; 1997; pp. 45-56; vol. 7.

* cited by examiner

*Primary Examiner*—David A Saunders
(74) *Attorney, Agent, or Firm*—Townsend and Townsend and Crew LLP

(57) ABSTRACT

This invention provides methods and kits for use in diagnosing genetically transmitted diseases that are associated with deficiencies in glycosylation of glycoconjugates such as glycoproteins, glycolipids, and proteoglycans. The methods and kits are also useful for monitoring the course of treatment of diseases that are associated with glycosylation disorders.

13 Claims, 17 Drawing Sheets

E-PHA BINDING TO GLYCOPROTEINS FROM SERUM OF CDGS PATIENTS

1. Control
2. Type 1a—died at 6
3. Type 1a—living
4. Type 4
5. Type 1b—before mannose
6. Type 1b—after mannose A) Flow cytometry and B) dot-blot analyses on blood from normal and CDGS Type II patient.

Core fucosylation of serum immunoglobulin M before and after initiation of fucose therapy

A

B

C

DIAGNOSIS OF HUMAN GLYCOSYLATION DISORDERS

CROSS-REFERENCES TO RELATED APPLICATIONS

This application is a continuation application claiming priority to U.S. application Ser. No. 09/857,233, filed Dec. 12, 2001, which is a U.S. National Phase Application, filed under 35 U.S.C. §371 of Patent Cooperation Treaty Application Number PCT/US99/28591, filed Dec. 1, 1999, which application claims the benefit of U.S. Provisional Application Nos. 60/114,174, filed Dec. 30, 1998; 60/113,680, filed Dec. 21, 1998; and 60/110,671, filed Dec. 2, 1998. Each of the aforementioned applications are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant Nos. DK48247 and RO1 GM55695, each awarded by the National Institutes of Health. The Government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

This invention pertains to the field of diagnosis of genetically transmitted diseases that are characterized by an abnormality in the glycosylation of proteins or other glycoconjugates.

BACKGROUND OF THE INVENTION

In 1980, Jaeken et al. (*Pediatric Research* 14:179) described a new neurological disorder in twin girls. Since then over 200 similar patients have been described, mostly in Northern Europe, but the syndrome is found in various countries. Patients present in the neonatal period with hypotonia, failure to thrive, and dysmorphic features including esotropia, inverted nipples, and subcutaneous fat over the suprapubic region. Severe mental and psychomotor retardation with hepatomegaly, cerebellar hypoplasia and brain stem atrophy are seen. Many have vomiting, diarrhea, coagulopathy, stroke-like episodes, pericardial effusions, seizures, and retinitis pigmentosa (McDowell and Gahl (1997) *Proc. Soc. Exp. Biol. Med.* 215: 145-157; Krasnewich and Gahl (1997) *Advances in Pediatrics* 44: 109-140; Jaeken et al. (1993) *Glycobiology* 3: 423-428; Kristiansson et al. (1998) *J. Pediatr. Gastroenterol. Nutr.* 27: 23-29). A comprehensive monograph describing clinical features, stages, progression and biochemical analysis appeared in 1991 (Jaeken et al. (1991) *Acta Paediatr. Scand. Suppl.* 375: 1-71).

The syndrome reported by Jaeken et al. was the first of a new group of multisystemic disorders caused by faulty glycosylation that is now emerging. These Carbohydrate-Deficient Glycoprotein Syndromes (CDGS) are usually neuropathies, but non-neurological forms of CDGS have appeared recently (Niehues et al. (1998) *J. Clin. Invest.* 101:1414-1420; de Koning et al. (1998) *Biochem Biophy Res Commun* 245:38-42; Jaeken et al. (1998) *Amer. J. Hum. Genet.* 62: 1535-1539). Some cases present with hypoglycemia, severe protein-losing enteropathies, persistent vomiting along with coagulopathy. All CDGS patients are believed to have primary defects that directly affect the N-glycosylation pathway.

The most commonly used method for diagnosing CDGS is a transferrin isoelectric focusing (IEF) test, which was originally used to screen for alcoholism. Serendipitously, the transferrin IEF test was found to be useful for diagnosing some of the CDGS disorders. The basis for this test is that transferrin usually has two complex-type N-linked oligosaccharide chains, each with two sialic acids, for a total of four negative charges. A few oligosaccharide chains have three sialic acids, yielding transferrin molecules with five and six negative charges. Any genetic or physiological condition that reduces the number of sugar chains on the proteins, or changes the structure of the sugar chains so they carry fewer sialic acids, will likely change the isoelectric point and the IEF pattern. Most known cases of CDGS result in loss of an entire sugar chain. A few patients make incomplete chains. Both give rise to partially carbohydrate deficient transferrin (CDT) with an altered IEF pattern. The transferrin IEF test forms the basis for biochemically dividing the CDG syndromes into four types (Henry et al. (1997) *J. Lab. & Clin. Med.* 129: 412-421; Stibler et al. (1993) *Neuropediatrics* 24: 51-52; Stibler et al. (1995) *Neuropediatrics* 26: 235-237; Jaeken et al. (1993) *J. Inherit. Metab. Dis.* 16: 1041). Analysis of the isoforms of other serum glycoproteins can also be used to diagnose CDGS. More than 40 different serum glycoproteins have been shown to have altered isoforms or decreased activities (Harrison et al. (1992) *Clin. Chem.* 38: 1390-1392; Henry et al. (1997) *J. Lab. & Clin. Med.* 129: 412-421; Stibler et al. (1998) *Scand. J. Clin. Lab. Invest.* 58: 55-61). These include antithrombin III (AT-III), factor XI and protein C.

Evidence suggests that the already identified CDG syndromes are just the tip of the iceberg of diseases and other conditions that are due to misglycosylations. For example, the preliminary findings by Murch et al. that symptoms and pathologies of inflammatory bowel disease are improved by providing N-acetylglucosamine to the patients are provocative (Murch et al. (1998) *British Society of Gastroenterology* (Abstract)). The mechanism, of course, is unknown, and neither "glycoscience" nor medicine have a data base that provides satisfactory explanations. Additional areas for further investigation for both clinicians and glycobiologists have been suggested (Gahl W A. (1997) *J. Lab. Clin. Med.* 129: 394-395; Kornfeld S (1998) *J. Clin. Invest.* 101: 1293-1295).

Approximately fifty percent of dysmorphic and dysfunctional children that appear at the pediatric clinic remain undiagnosed throughout childhood and adult life. Many are broadly diagnosed with "seizure disorders," "cerebral palsy," or as "mentally retarded." Some have early deaths. Aberrant glycosylation is seldom suspected as a cause of these conditions or other human diseases, even though approximately one percent of human genes encode proteins that produce and/or recognize oligosaccharides.

The discovery and treatment of additional diseases that are associated with deficiencies in glycosylation has been hampered by a lack of efficient and effective diagnostic tests. The IEF assays of transferrin and other serum glycoproteins suffer from significant drawbacks as diagnostic tools for CDGS and other glycosylation disorders. For example, a specific IEF pattern does not define a specific mutation, as any one of several different defects can give rise to the same IEF pattern. In the case of transferrin, three different biochemical defects all yield the same "Type I" transferrin IEF pattern. A second disadvantage is that transferrin contains only a small number of oligosaccharide structures, so the IEF test can identify only a small fraction of glycosylation-deficient states. Moreover, temporary physiological conditions such as uncontrolled fructosemia, galactosemia, and recent heavy alcohol consumption can also disturb glycosylation and produce abnormal transferrin IEF patterns (Stibler et al. (1997) *Acta Paediatrica* 86: 1377-1378; Jaeken et al. (1996) *Pediatric Research* 40:764-766). Yet another major shortcoming is that fewer than five diagnostic laboratories in the US analyze serum transferrin IEF mobility.

The lack of adequate methods for diagnosing glycosylation disorders is particularly tragic in that once recognized, life-threatening defects in glycosylation can be treated and sometimes cured. In at least one case, for example, a CDGS patient was successfully treated with a dietary therapy of the sugar mannose. Therefore, a need exists for simple, efficient, and accurate methods for diagnosing glycosylation disorders. The present invention fulfills this and other needs.

BRIEF SUMMARY OF THE INVENTION

The present invention provides methods and kits for diagnosing a genetically transmitted glycosylation disorder in a mammal. The methods involve providing a sample from the mammal that contains a plurality of glycoconjugates and contacting the sample with a diagnostic reagent. The diagnostic reagents are typically either or both of two types. The first type binds to a glycoconjugate that has an oligosaccharide determinant that: i) is present on glycoconjugates in a sample obtained from a mammal that has the glycosylation disorder, and ii) is not present on glycoconjugates in a sample obtained from a mammal that does not have the glycosylation disorder. The second type of diagnostic reagent binds to a glycoconjugate that has an oligosaccharide determinant that is: i) is present on glycoconjugates in a sample obtained from a mammal that does not have the glycosylation disorder, and ii) is not present on glycoconjugates in a sample obtained from a mammal that has the glycosylation disorder. The diagnosis of the glycosylation disorder is obtained by determining whether the diagnostic reagent binds to the glycoconjugates in the sample. The presence of the glycosylation disorder in the mammal is indicated by the binding to the sample of a diagnostic reagent of the first type, or the absence of binding to the sample of a diagnostic reagent of the second type. The glycoconjugates can include, for example, glycoproteins, glycolipids, and proteoglycans. Significantly, the diagnostic methods of the invention are effective even when the glycoconjugates are unpurified.

The diagnostic methods and kits of the invention can be used for diagnosing a wide variety of genetically transmitted conditions that are associated with a glycosylation disorder. For example, the methods are useful for diagnosing alcoholism, Carbohydrate-Deficient Glycoprotein Syndromes (CDGS), and other conditions that are known to be associated with glycosylation disorders. In addition, the methods and kits can be used to identify other diseases and conditions for which an association with glycosylation abnormalities is not yet known or even suspected.

In another embodiment, the invention provides methods for monitoring the course of treatment of a glycosylation disorder in a mammal. These methods involve obtaining a first sample which comprises a plurality of glycoconjugates from the mammal, administering to the mammal a potential treatment regime for the glycosylation disorder, and then obtaining at least a second sample which comprises a plurality of glycoconjugates from the mammal. The first and second samples are then contacted with a diagnostic reagent and the amount of diagnostic reagent that binds to the two samples is compared. The diagnostic reagents are generally of one of two types. A first type of diagnostic reagent binds to a glycoconjugate that has an oligosaccharide determinant that: i) is present on glycoconjugates in a sample obtained from a mammal that has the glycosylation disorder, and ii) is not present on glycoconjugates in a sample obtained from a mammal that does not have the glycosylation disorder. A second type of diagnostic reagent binds to a glycoconjugate that has an oligosaccharide determinant that is: i) is present on glycoconjugates in a sample obtained from a mammal that does not have the glycosylation disorder, and ii) is not present on glycoconjugates in a sample obtained from a mammal that has the glycosylation disorder. An effective treatment regime is indicated by decreased binding of a diagnostic reagent of the first type, or by increased binding of a diagnostic reagent of the second type, to the second sample relative to the first sample.

The invention also provides methods and kits for detecting in a mammal a genetically transmitted immune system dysfunction that is associated with a glycosylation disorder. These methods involve contacting a sample of glycoconjugates from the mammal with at least one diagnostic reagent. The diagnostic reagents are generally one of two types. A first type of diagnostic reagent binds to a glycoconjugate that has an oligosaccharide determinant that: i) is present on glycoconjugates in a sample obtained from a mammal that has the immune system dysfunction, and ii) is not present on glycoconjugates in a sample obtained from a mammal that does not have the immune system dysfunction. The second type of diagnostic reagent binds to a glycoconjugate that has an oligosaccharide determinant that is: i) is present on glycoconjugates in a sample obtained from a mammal that does not have the immune system dysfunction, and ii) is not present on glycoconjugates in a sample obtained from a mammal that has the immune system dysfunction. The presence of the immune system dysfunction in the mammal is indicated by binding to the sample of a diagnostic reagent of the first type, or the absence of binding of a diagnostic reagent of the second type. These methods and kits are useful for diagnosing immune system dysfunctions such as B lymphocyte dysfunction, cytotoxic T cell deficiency, and myeloid deficiency, among others.

Additional embodiments of the invention provide chimeric or transgenic nonhuman mammals that contain cells having a defect in a gene which encodes an enzyme involved in biosynthesis of an oligosaccharide determinant of a glycoconjugate. In some embodiments, the defect reduces or eliminates expression of the gene that encodes the enzyme, while in other embodiments the defect results in expression of an enzyme that has reduced activity. The enzyme can be, for example, one that catalyzes the formation of a glycosidic linkage (e.g., a glycosyltransferase), or one that catalyzes the cleavage of a glycosidic linkage (e.g., a glycosidase).

DEFINITIONS

The following abbreviations are used herein:
Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
Sia (NeuAc)=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

The term "isolated" is meant to refer to material which is substantially or essentially free from components which normally accompany a compound as found in its native state. Thus, an isolated compound does not include materials normally associated with its in situ environment. Typically, isolated compounds are at least about 80% pure, usually at least about 90%, and preferably at least about 95% pure. In the case of proteins, for example, purity can be measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The phrases "specifically binds to an oligosaccharide determinant" or "specifically reactive with an oligosaccharide determinant", when referring to an antibody, lectin, or other binding component, refers to a binding reaction which is determinative of the presence of an oligosaccharide determinant in the presence of a heterogeneous population of proteins and other biologics. Thus, under designated assay conditions, the specified antibodies, lectins, or other binding components bind preferentially to a particular oligosaccharide determinant and do not bind in a significant amount to other oligosaccharides present in the sample. Specific binding to an oligosaccharide determinant under such conditions requires an antibody, lectin, or other binding component that is selected for its specificity for a particular oligosaccharide determinant. A variety of immunoassay or related formats can be used to select binding components that are specifically reactive with a particular oligosaccharide determinant. For example, solid-phase ELISA immunoassays are routinely used to select monoclonal antibodies specifically immunoreactive with a particular antigen. See Harlow and Lane (1988) *Antibodies, A Laboratory Manual*, Cold Spring Harbor Publications, New York, for a description of immunoassay formats and conditions that can be used to determine specific immunoreactivity.

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al. (1990) *J. Biol. Chem.* 265: 21811-21819. Also included are 9-substituted sialic acids such as a 9-O-C1-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25-40; *Sialic Acids: Chemistry, Metabolism and Function*, R. Schauer, Ed. (Springer-Verlag, New York (1992). The synthesis and use of sialic acid compounds in a sialylation procedure is disclosed in international application WO 92/16640, published Oct. 1, 1992.

The term "transgenic" refers to a cell that includes a specific genetic modification that was introduced into the cell, or an ancestor of the cell. Such modifications can include one or more point mutations, deletions, insertions, or combinations thereof. When referring to an animal, the term "transgenic" means that the animal includes cells that are transgenic, and descendants of such animals. An animal that is composed of both transgenic and non-transgenic cells is referred to herein as a "chimeric" animal.

As used herein, a "substantial reduction" or a "substantial increase" in the binding of a diagnostic reagent to a sample refers to a reduction or increase, respectively, of at least about 30% in the test sample compared to a control. Preferably, the reduction or increase will be at least about 50%, more preferably at least about 75%, and most preferably binding levels will be reduced or increased by at least about 90% in a test sample compared to a control. Note that a reduction or increase in diagnostic reagent binding can be associated with either the presence of a defect in the glycosylation pathway, or with the absence of such defect, depending upon the particular diagnostic reagent whether the defective enzyme is involved in making the oligosaccharide determinant or is involved in converting the oligosaccharide determinant into another structure that is not recognized by the diagnostic reagent.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

BRIEF DESCRIPTION OF THE DRAWINGS

In FIG. 9A, the wild type C2GlcNAcT genomic locus was used in conjunction with the pflox vector to construct a targeting vector in which the single exon open reading frame was flanked by loxP sites (C2 GlcNAcT$^{F[tkneo]}$). Restriction enzyme sites indicated are Bam HI (B), Bgl II (Bg), Hind III (H), Not I (N), and Xba I (X). Transient Cre expression in C2 GlcNAcT-targeted ES cells resulted in subclones isolated with a C2 GlcNAcT$^\Delta$ (systemic-null) or C2 GlcNAcT$^F$ (conditional-null) mutation (FIG. 9B). FIG. 9C shows a Southern blot analysis of a Bam HI/Bgl II digest of ES cell DNA probed with a loxp probe, which confirmed the expected structures. Wild type RI ES cell DNA showed no hybridization with the loxP probe. Three loxP sites are present in a targeted parental clone (156), one loxP site is present in each of two C2 GlcNAcT$^\Delta$ subclones (156.24 and 156.29) and two loxP sites are present in the C2 GlcNAcT$^F$ subclone (156.34). In the right panel, tail DNA from a heterozygous mating of progeny from a C2 GlcNAcT$^\Delta$ chimera digested with Hind III and probed with the genomic probe indicates the 6.5 kb wild type allele and the 3.7 kb mutant allele.

In FIG. 10A, tissues normally expressing C2 GlcNAcT activity were assayed for enzyme activity in wild type, heterozygous and homozygous null mice. Results represent one of three similar experiments. FIG. 10B shows an oligosaccharide analysis that was carried out on splenocytes of wild type and C2 GlcNAcT$^{\Delta/\Delta}$ mice. [$^3$H]-Glucosamine labeled O-glycans were isolated and subjected to Bio-Gel P-4 gel filtration (upper panels). The fractions containing sialylated oligosaccharides (peaks 1 and 2) were combined, desialylated and subjected to HPLC (lower panels). Peaks 1, 2, 3, 4, and 5 indicate the elution positions of disialylated forms of Galβ1-3(Galβ1-4GlcNAcβ1-6)GalNAcOH and Galβ1-3GalNAcOH (peak 1) and monosialylated forms of Galβ1-3(Galβ1-4GlcNAcβ1-6)GalNAcOH and Galβ1-3GalNAcOH (peak 2), Galβ1-3(Galβ1-4GlcNAcβ1-6)GalNAcOH (peak 3), Galβ1-3GalNAcOH (peak 4) and GalNAcOH (peak 5). In the experiment shown in FIG. 10C, splenocytes were double-stained with mAbs recognizing CD22 and the B cell specific form of CD45 (B220) or CD22 and all CD45 isoforms (30-F11). Cells were also double-stained with mAbs recognizing the 115 (S7) and 130 (1B11) kD glycoforms of CD43 and subjected to flow cytometric analysis. Myeloid cells were gated by forward and side scatter.

FIG. 12A: Purified peripheral blood leukocytes were stained with Gr-1 and either the P- or E-selectin-IgM chimera for 30 min at 4° C. A goat anti human secondary was used to detect the IgM chimeras and live cells were gated on the Gr-1 positive population when subjected to FACS analysis. Cells stained in the presence of EDTA acted as the controls. Data are representative of 4 separate experiments. FIG. 12B: Peripheral blood leukocytes were stained with Gr-1 and monoclonal or polyclonal antibodies directed against leukocyte adhesion molecules (CD11a, CD11b, CD18) or the selectin counter-receptors (CD24, CD62L, PSGL-1). The panel is 1 of 3 similar experiments in which data collected represents 2500 events gated on Gr-1 positive cells. FIG. 12C: Peripheral blood neutrophils from wild type, C2 GlcNAcT null and FucT-VII null mice were infused into a flow chamber coated with immobilized E-, P- or L-selectin IgG chimeras. Static adhesion of cells was recorded after stopping the flow for 3 minutes and rolling counts were recorded on video after application of specific shear forces. The number of independent measurements is indicated in parentheses. Data represent the mean± SEM. Site densities were as follows: E-selectin-IgG, 63 molecules per square micrometer; L-selectin IgG, 2,840 molecules per square micrometer; P-selectin-IgG, 1,469 molecules per square micrometer.

FIG. 13A: Mesenteric and peripheral (brachial and axillary) lymph nodes and Peyer's patch aggregates were isolated from wild type or C2 GlcNAcT null mice. Lymphocytes recovered from each organ were quantitated manually using a hemocytometer. Seven animals of each genotype were analyzed and results are presented as means± SEM. Frozen sections of peripheral lymph nodes stained with hematoxylin and eosin were photographed at 25× magnification. FIG. 13B: For L-selectin immunohistochemistry, frozen sections of peripheral lymph nodes from wild type (left panels) or C2 GlcNAcT$^{\Delta/\Delta}$ (right panels) mice were stained with an L selectin IgM immunohistochemical probe or with the MECA 79 antibody. FIG. 13C: In lymphocyte homing studies, wild type lymphocytes were injected into the tail vein of wild type or C2 GlcNAcT null mice. CMFDA positive lymphocytes in mesenteric and peripheral (brachial and axillary) lymph nodes, and Peyer's patches from four mice of each genotype were analyzed by flow cytometry (100,000 events). Data are presented as the mean± the SEM. The slight decrease in homing to Peyer's patch tissue was not statistically significant (p=0.38).

FIG. 15A (left panel) presents an analysis of bone marrow lymphocytes for cell surface expression of IgM, CD24 (HSA), CD43 (S7), and B220 by flow cytometry. No deviations were observed in ST6Gal-deficient mice among the percentages (denoted in parentheses) of pro-B cells (B22$^{lo}$ CD43(S7)+, gate a (Hardy et al. (1991) J. Exp. Med. 173: 1213-1225)), pre-B cells (B220$^{lo}$ HSA$^{hi}$, gate b (Carsetti et al. (1995) J. Exp. Med. 181: 2129-2140)), immature B cells (B220$^{lo}$ IgM$^{int}$, gates b and c (Carsetti et al., supra.)), transitional B cells (B220$^{lo-hi}$ IgM$^{hi}$, gate d (Carsetti et al., supra.)), and mature B cells (B220$^{hi}$ gM$^{int}$, gate e, and B220$^{hi}$ HSA$^{lo}$, gate f (Carsetti et al., supra.)). Percentages shown are the mean of four different analyses with calculated Student's t test, P>4 for all genotypic comparisons indicating no significant variations. FIG. 15A (right panel) shows that ST6Gal-deficient splenic B cells exhibited reductions in cell surface CD22 and IgM, but not in HSA. Reductions in cell surface IgM levels were found to be at 65±20% of controls (Student's t test; P<0.001) and CD22 levels at 38±9% of controls (P<0.001) as determined by comparisons of peak fluorescence (n=8).

FIG. 15B shows that Sia6LacNAc-deficient splenic B cells expressed normal levels of activation markers (CD44, B7.2, and I-A$^b$) and CD40. Dotted lines represent fluorescence of cells stained using an isotype control antibody (n=8).

FIG. 15C presents measurements of serum Ig levels in 4-6 month old unimmunized littermates of indicated genotypes. The median Ig levels are depicted as horizontal bars. Genotypes of 4-6 month old mice are provided on the x-axis. Points represent measurements from single and distinct animals. Results revealed a 63% reduction (P>0.001) in circulating IgM and no statistically significant reduction in IgA or IgG.

FIG. 16A shows the structure of the wild-type mouse ST3Gal I gene as found on genomic clone 129 Sv/J, and the pflox construct that was used to make a targeting vector as shown in FIG. 16B. Upon homologous recombination with the ST3Gal I$^{wt}$ locus in mouse ES cells, as shown in FIG. 16B, ES cells heterozygous for the ST3Gal I$^{F[tkneo]}$ construct were obtained. Cre-mediated recombination with ganciclovir selection resulted in two types of deletions as shown in FIG. 16C, the ST3Gal I− deletion, which resulted from a Type 1 deletion lacks exon 2 of the ST3 Gal I gene, and the ST3Gal I$^F$ construct which resulted from a Type 2 deletion.

DETAILED DESCRIPTION

Figure 1:
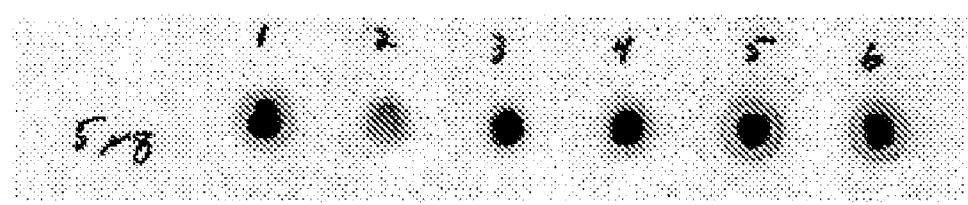
FIG. 1 shows variations in E-PHA binding to glycoproteins from serum of CDGS patients.

The present invention provides novel methods and kits for diagnosing genetically transmitted diseases and other conditions that are associated with abnormal glycosylation of glycoconjugates such as glycoproteins, glycolipids, and proteoglycans. These disorders typically are a result of abnormal expression or activity of an enzyme that is involved in a glycosylation pathway. The diagnostic methods of the invention involve contacting a sample from a human or other mammal with a diagnostic reagent that specifically and differentially binds to a glycoconjugate depending on the glycosylation state of the glycoconjugate. For example, the diagnostic reagent can bind to an oligosaccharide determinant on the glycoconjugate, the presence or absence of which is diagnostic for the glycosylation disorder. Alternatively, the diagnostic reagent can bind to a polypeptide that, due to the glycosylation disorder, is not glycosylated at an amino acid position to which an oligosaccharide is attached when the polypeptide is produced in a mammal that does not exhibit the glycosylation disorder of interest.

The invention is based on part upon the surprising discovery that one can uniquely detect changes in glycosylation that result directly from a mutagenic event in a gene that encodes an enzyme involved in the glycosylation pathway. The detection is accomplished by using one or more of various lectins, antibodies, and other binding moieties that are specific for particular oligosaccharide determinants that, depending on the presence or absence of the glycosylation disorder, are found on glycoconjugates obtained from a mammal. Alternatively, the diagnostic reagents can be specific for other changes in glycoconjugate structure that arise as a result of the glycosylation disorder (e.g., a conformation change of a glycoconjugate or the masking/unmasking of an epitope by the presence or absence of an attached oligosaccharide). The detection can be accomplished in a sample that contains a mixture of glycoconjugates (e.g. whole blood and tissue biopsies) from an intact mammal without the need to identify or purify any particular protein, lipid, or other glycoconjugate upon which the glycosylation change occurs.

The methods of the invention can detect changes in glycosylation that are diagnostic of genetic deficiency and diseases that result from glycosylation defects. In contrast, changes in glycosylation that have been observed in, for example, cancer, are sporadic epigenetic effects of the oncogenic mutation, and are therefore not diagnostic of any disease, including cancer. Furthermore, this invention shows the occurrence of surprisingly unique patterns of lectin reactivity can be diagnostic for specific mutagenic defects in the glycosylation pathway. Mutation of genes that do not encode enzymes within the glycosylation pathway (e.g., cancer) may produce sporadic glycosylation changes among individuals that are not diagnostic of any specific disease or a genetic deficiency in any specific gene, again unlike this invention.

The diagnostic methods and kits of the invention are useful for determining whether a patient or other mammal exhibits a glycosylation disorder. The methods and kits are useful not only for those conditions that are already known to be associated with a glycosylation disorder, but also for conditions for which the underlying defect is not yet known. In such cases, the use of the methods and kits of the invention will aid in determining whether these conditions are associated with a glycosylation disorder. In addition to being useful for diagnosing glycosylation disorders, the methods and kits of the invention are useful for monitoring the course of treatment of a condition that is associated with a glycosylation defect. For example, some glycosylation disorders are treatable by administering a sugar to a patient. By monitoring the ability of a diagnostic reagent to bind to a sample obtained from the patient at various time intervals, one can determine whether the treatment method is efficacious.

Diagnostic Methods

The present invention provides methods and kits for diagnosing a genetically transmitted glycosylation disorder in a mammal. The methods of the invention are performed on samples obtained from a mammal suspected of having a glycosylation disorder. The samples, which include a plurality of glycoconjugates, are contacted with a diagnostic reagent that consists of a binding component and, often, a label. The ability of the diagnostic reagent to bind to the glycoconjugates in the sample is indicative of the presence or absence of the glycosylation disorder.

A. Diagnostic Reagents

Figure 17:
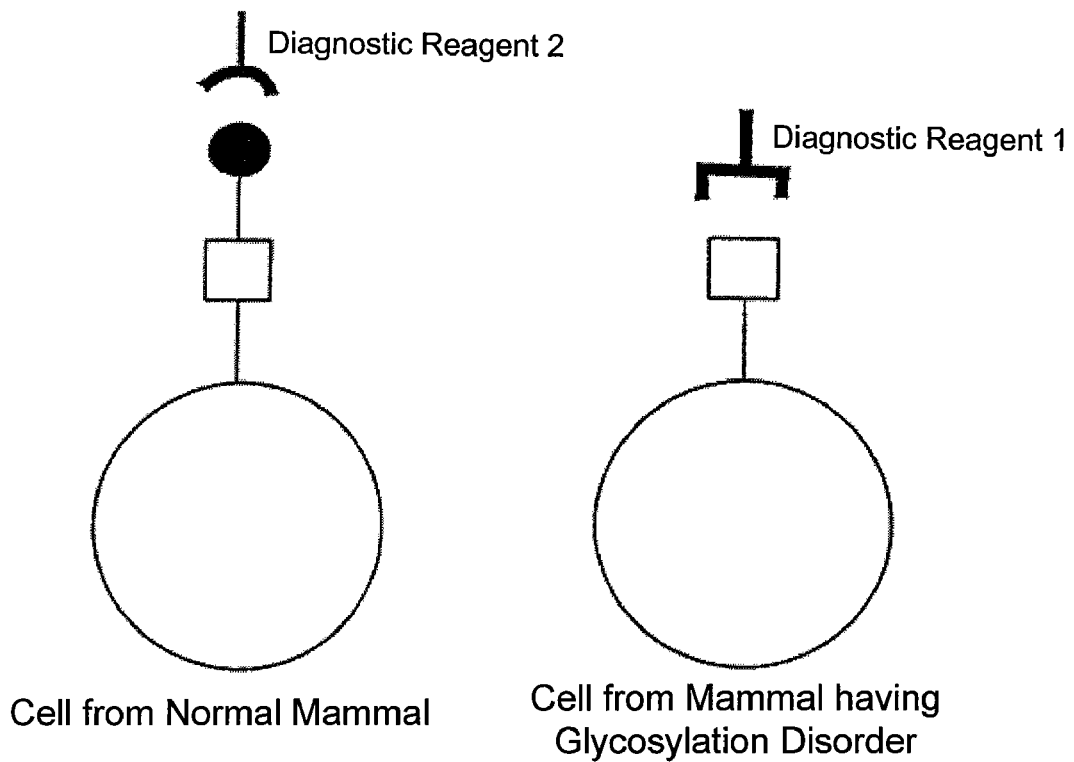
FIG. 17 shows an illustration of two types of diagnostic reagent that are useful in the methods and kits of the invention. In the illustrated example, the glycosylation disorder is due to a deficiency in a glycosyltransferase that, if present, would link a saccharide moiety (shown as ●) to an acceptor saccharide (shown as □). Diagnostic reagent 2 can bind to the oligosaccharide determinant formed by the linkage of the saccharide moiety to the acceptor saccharide, but cannot bind to the acceptor saccharide alone. Thus, binding of this diagnostic reagent to a sample is indicative of a lack of the glycosylation disorder. In contrast, diagnostic reagent 1 can bind to the acceptor saccharide alone, but not to an acceptor saccharide that has been modified by addition of the saccharide moiety. Accordingly, binding of diagnostic reagent 1 to a sample indicates that the mammal from which the sample was obtained has the glycosylation disorder.

The diagnostic methods of the invention employ diagnostic reagents that can specifically bind to a particular oligosaccharide structure or polypeptide conformation that is diagnostic for the glycosylation disorder under consideration. Two general categories of diagnostic reagents are provided. The first type of diagnostic reagent binds to a glycoconjugate that has an oligosaccharide determinant that: i) is present on glycoconjugates in a sample obtained from a mammal that has the glycosylation disorder, and ii) is not present on glycoconjugates in a sample obtained from a mammal that does not have the glycosylation disorder. Binding of this type of diagnostic reagent to a sample is indicative of the presence of the glycosylation disorder in the mammal. An example of this type of diagnostic reagent is shown in FIG. 17 as Diagnostic Reagent 1. In this example, the glycosylation disorder results in a failure to attach a saccharide moiety to an acceptor sugar. The diagnostic reagent can bind to the acceptor sugar if unmodified, but not if the saccharide moiety is attached. Thus, the presence of the disorder is indicated by the binding of the diagnostic reagent to the sample.

The second general type of diagnostic reagent binds to a glycoconjugate that has an oligosaccharide determinant that is: i) is present on glycoconjugates in a sample obtained from a mammal that does not have the glycosylation disorder, and ii) is not present on glycoconjugates in a sample obtained from a mammal that has the glycosylation disorder. FIG. 17 shows an example of this type of diagnostic reagent as Diagnostic Reagent 2. Again, the glycosylation disorder causes a failure to attach a saccharide moiety to an acceptor saccharide. However, the presence of the glycosylation disorder is indicated by the absence of binding to the sample.

The diagnostic reagents can bind directly to an oligosaccharide determinant, or can bind to other parts of a glycoconjugate. For example, the glycosylation disorder might involve the absence of a particular enzyme that, if it were present, would add a saccharide residue to the oligosaccharide structure to which the diagnostic reagent binds, with the resulting change in the structure preventing the diagnostic reagent from binding to a sample from a mammal that has the glycosylation disorder. In other embodiments, one can use a diagnostic reagent that can bind to a non-carbohydrate portion of a glycoconjugate when a particular oligosaccharide structure is not present on the non-carbohydrate portion, but cannot bind to the same non-carbohydrate portion if the oligosaccharide structure is attached to the glycoconjugate. For example, the presence of the attached oligosaccharide structure can change the conformation of the glycoconjugate or mask an epitope, thus affecting binding of the diagnostic reagent.

The diagnostic reagents used in the methods and kits of the present invention generally include at least two components: a binding component that can specifically bind to the oligosaccharide structure that is diagnostic for the particular disease, and a label.

1. Binding Components.

The binding components used in the diagnostic reagents of the invention can differentially bind to a glycoconjugate depending upon the glycosylation state of the glycoconjugate. The presence or absence of binding is associated with a defect in a gene that encodes an enzyme involved in the synthesis of an oligosaccharide determinant that is normally attached to the glycoconjugate.

To identify appropriate binding components for a particular defective enzyme, one can use a test system in which the activity of the glycosylation enzyme of interest is reduced or eliminated. For example, a "knockout" transgenic or chimeric animal can be constructed in which the gene that encodes the enzyme is mutated so that the enzyme is not expressed, or if expressed, is not active. Methods for constructing suitable knockout animals are described below. Another test system can involve treating a test animal with an inhibitor of the glycosylation enzyme. One or more samples from the test animal are then tested against one or more potential binding components. Those binding components that do not bind to samples from normal animals but bind to those in which the enzyme is absent, or vice versa, are suitable for diagnosing a deficiency in that enzyme.

In some presently preferred embodiments, the binding components are lectins. Many lectins are known and are commercially available. Table 1 provides a list of glycosyltransferases, together with a list of lectins that are diagnostic for a deficiency in activity of the corresponding glycosyltransferases. In the absence of the glycosyltransferase, the oligosaccharide structure to which the respective lectin would bind is not synthesized.

TABLE 1

Lectin and the corresponding glycosyltransferases upon which lectin binding depends.

| Lectin | Glycosyltransferases required for binding |
|---|---|
| *Amaranthus caudatus* (ACL, ACA) | beta 1-3 galactosyltransferase(s) |
| Concanavalin A | α-mannosyl transferases |
| *Datura stramonium* (DSA) | beta 1-4 N-acetylgalactosaminyltransferase(s) |
| *Erythrina cristagalli* (ECL, ECA) | beta 1-4 galactosyltransferase(s) |
| *Euonymus europaeus* (EEL) | alpha 1-3 galactosyltransferase(s) |

TABLE 1-continued

Lectin and the corresponding glycosyltransferases upon which lectin binding depends.

| Lectin | Glycosyltransferases required for binding |
|---|---|
| *Griffonia (Bandeiraea) simplicfolia* II (GSL II, BSL II) | N-acetylglucosaminyltransferase(s) |
| Jacalin | beta 1-3 galactosyltransferase(s) |
| *Lycopersicon esculentum* (Tomato Lectin) | N-acetylglucosaminyltransferase(s) |
| *Maackia amurensis* I (MAL I) | beta 1-3 galactosyltransferase(s) |
| *Maackia Amurensis* II (MAL II) | alpha 2-3 sialyltransferase(s), ST3Gal I-IV |
| *Maclura pomifera* (MPL) | alpha N-acetylgalactosaminyltransferase(s) |
| Peanut agglutinin (PNA) | beta 1-3 galactosyltransferase(s) |
| Erythroagglutinin, *Phaseolus vulgaris* (E-PHA) | N-acetylglucosaminyltransferase II alpha-mannosidase-II (erythrocytes) |
| Leucoagglutinin, *Phaseolus vulgaris* (L-PHA) | N-acetylglucosaminyltransferase V |
| *Psophocarpus tetragonolobus* I (PTL I, WBA I) | alpha galactosaminyltransferase(s) |
| *Ricinus communis* Agglutinin I and II (RCA I and RCA II) | galactosyltransferase(s) and N-acetylgalactosaminyltransferase(s) |
| *Sambucus nigra* (SNA, EBL) | alpha 2-6 sialyltransferase(s), ST6Gal, ST6GalNAc I-III |
| *Sophora japonica* (SJA) | galactosyltransferase(s) N-acetylgalactosaminyltransferase(s) |
| Soybean Agglutinin (SBA) | N-acetylgalactosaminyltransferase(s) |
| *Ulex europaeus* Agglutinin I (UEA I) | alpha fucosyltransferase(s) |
| *Vicia villos* (VVL, VVA) | N-acetylgalactosaminyltransferase(s) |
| Wheat germ agglutinin (WGA) | N-acetylglucosaminyltransferase(s) |
| *Wisteria floribunda* (WFA, WFL) | N-acetylgalactosaminyltransferase(s) |

Another type of binding component that can be used in the diagnostic reagents of the invention is antibodies that specifically bind an oligosaccharide determinant, the presence or absence of which is associated with a defect in an enzyme involved in the glycosylation pathway. Several oligosaccharide-specific antibodies are known to those of skill in the art. Antibodies which are specific for a particular oligosaccharide determinant may be produced by a variety of means. The production of non-human monoclonal antibodies, e.g., murine, lagomorpha, equine, etc., is well known and may be accomplished by, for example, immunizing the animal with a glycoprotein from an animal which has the glycosylation defect of interest. Antibody-producing cells obtained from the immunized animals are immortalized and screened, or screened first for the production of antibody which detects the glycoprotein from the defective animal but does not bind to the glycoprotein from a control animal. For a discussion of general procedures of monoclonal antibody production, see, Harlow and Lane, *Antibodies, A Laboratory Manual* (1988) Cold Spring Harbor Laboratory.

Binding components can also be obtained from antibodies or other binding moieties that bind or do not bind to a protein depending on its glycosylation state. For example, a binding component might bind to a protein that is not glycosylated at a particular amino acid position, but not to the same protein when the protein is glycosylated at that amino acid. Such binding components can bind to the polypeptide itself, rather than to an oligosaccharide. The absence of an oligosaccharide at a particular position can, for example, change the conformation of the polypeptide, unmask an epitope, or have another effect that results in differential binding of the binding component. One can obtain such binding components by, for example, immunizing an animal with a peptide or polypeptide that includes an amino acid sequence at which the protein from which the peptide is obtained would be glycosylated if produced in an animal that does not exhibit a particular glycosylation defect of interest.

Glycosyltransferases themselves, in particular the acceptor binding domain of a glycosyltransferase, are also useful as binding moieties in the diagnostic assays of the invention. In the absence of a particular sialyltransferase, for example, the concentration of acceptor moieties tends to increase. As an example, a deficiency of ST6Gal sialyltransferase causes a dramatic increase in terminal galactose residues (i.e., Galβ1, 4GlcNAc-) on B cells. Thus, one can use the ST6Gal sialyltransferase as a detection moiety to determine whether ST6Gal is deficient in the cells. An ST3Gal transferase, or other glycosyltransferase that recognizes terminal galactose residues can be used similarly as a detection moiety.

2. Labels.

In typical embodiments, the binding components are labeled with a detectable label. The detectable labels can be primary labels (where the label comprises an element that is detected directly or that produces a directly detectable element) or secondary labels (where the detected label is attached to a second binding component that can bind to the binding component that binds to the oligosaccharide determinant. An introduction to labels, labeling procedures and detection of labels is found in Polak and Van Noorden (1997) *Introduction to Immunocytochemistry,* 2nd ed., Springer Verlag, NY and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to a component of the detection assay (e.g., the binding component for the particular oligosaccharide determinant) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which can be detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4ClN), which can be detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

B. Test Samples

The diagnostic methods of the invention are carried out on one or more samples from the human or other mammal. The samples can be any cell type or fluid that includes glycoconjugates. Particularly suitable samples include, for example, serum, plasma, whole blood, erythrocytes, leukocytes, urine, cerebrospinal fluid, tears, sweat, sputum, mucus membrane, or tissue biopsies taken from the skin, intestine, liver, kidney, lung, and the like.

Because a deficiency in an enzyme involved in a glycosylation pathway may or may not be reflected in a change in an oligosaccharide determinant on all types of samples, it is often desirable to test several samples from the mammal.

In situations in which a particular glycosylation deficiency is suspected due to, for example, clinical manifestations of a disease that is potentially associated with a deficiency in the synthesis of a particular oligosaccharide determinant, one can use a test system is used to identify appropriate samples for testing prior to diagnosis of an individual patient. For example, several types of sample from a knockout mouse that is defective for a particular glycosylation-associated gene can be tested with diagnostic reagents that, based on the oligosaccharide structure influenced by the enzyme, are expected to be suitable. Those samples for which a difference in binding is observed compared to the corresponding sample from a non-knockout control are then used as the test sample in the actual diagnostic assay.

In additional embodiments, the methods of the invention are useful for screening for glycosylation disorders where no particular enzymatic defect is evident in advance. These embodiments involve testing several samples from the patient. Each sample is tested with a panel of diagnostic reagents, each of which is associated with a particular enzymatic defect as determined as described above. By comparing the results obtained for the patient samples with binding of the diagnostic reagent to a panel of corresponding samples from a source that does not exhibit a glycosylation disorder, one can determine which, if any, of the glycosylation steps is defective.

C. Assay Formats

The invention provides methods and kits for determining whether a human or other mammal has a glycosylation disorder that results from a defect in a gene that encodes an enzyme involved in the pathway by which glycoconjugates are glycosylated. The methods involve 1) obtaining one or more samples from the patient, 2) testing the samples with a diagnostic reagent, or a panel of diagnostic reagents, to determine whether any differences are observed between the binding of the diagnostic reagent to the samples from the patient compared to binding of the diagnostic reagent to a corresponding sample from a "normal" control. If desired, one can confirm a positive result of the method which indicates a deficiency in an enzyme involved in glycosylation by assaying for the presence or absence of enzymatic activity.

Any of several assay formats known to those of skill in the art are suitable for testing the samples for ability to bind the diagnostic reagents (see, e.g., Harlow and Lane, supra.). For example, dot blots or other types of assay in which the sample is immobilized on a solid support and then contacted with the diagnostic reagent are suitable. An illustrative assay could involve obtaining a sample from a mammal (e.g., blood, serum, plasma, or other tissue), determining the protein concentration of the sample using a suitable assay (e.g., Bradford or Lowry), and dotting equivalent protein amounts onto a solid support such as nitrocellulose. The blots are then incubated with the diagnostic reagents which are at specific concentrations (a few ng/ml to a few µg/ml) and are then washed briefly. In some embodiments, a label is directly attached to the diagnostic reagent. In other embodiments, the diagnostic reagent is detected by contacting with a secondary detection reagent (e.g., goat anti-biotin-horseradish peroxidase), followed by a wash. The label is then detected by methods known to those of skill in the art (e.g., chemiluminescence, calorimetric detection systems, and the like). This assay and the following assay are merely illustrative, and modifications will be readily apparent to those of ordinary skill in the art.

Flow cytometry provides another assay format that can be used with the methods of the invention. An illustrative assay involves obtaining one or more samples from the human or other mammal to be tested (e.g., blood, plasma, serum, or other tissue samples) and incubating the samples with the diagnostic reagent. The diagnostic reagent will preferably include a moiety (e.g., biotin) that can bind to a particular ligand that is used for to attach the fluorescent label (e.g., streptavidin-FITC). After incubation with the diagnostic reagent for an appropriate period of time and under appropriate conditions (e.g., 30 minutes at room temperature or on ice in physiologic saline (with $Ca^{2+}$ and $Mg^{2+}$ as necessary) buffered to pH 7. Cells are washed and the detection system (e.g., streptavidin-FITC) is applied. Cells are then analyzed by flow cytometry.

Kits for Diagnosing Glycosylation Disorders

The present invention also provides kits and assay systems that are useful for diagnosing glycosylation disorders according to the methods described herein. The kits can include one or more detection reagents, with or without labels. Also included in the kits can be a suitable membrane or other solid support, preferably in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein. A container for one or more of the above components can also be included in the kits.

In some embodiments, the kits will contain a panel of diagnostic reagents. Such kits are useful for detecting a disorder for which the underlying glycosylation defect is unknown or incompletely characterized. By testing one or more samples from a human or other mammal that exhibits the disorder with a series of diagnostic reagents, each of which is useful for detecting the presence or absence of a specific oligosaccharide determinant, one can identify a likely candidate for the glycosylation defect. The panel of diagnostic reagents are, in some embodiments, immobilized on a solid support.

Use of the Diagnostic Methods and Kits to Diagnose Diseases Associated with Glycosylation Defects The methods and kits of the invention are useful for diagnosing, and monitoring the efficacy of treatment for, many diseases that are associated with a genetic defect that results in misglycosylation of one or more glycoconjugates in the patient. For example, one can detect changes in glycosylation that result from a deficiency in one or more genes that encode enzymes involved in glycosylation. Such enzymes include, for example, oligosaccharyltransferase, α-glucosidase I, α-glucosidase II, ER α1,2-mannosidase, N-acetylglucosaminyl-phosphotransferase, N-acetylglucosamine-1-phosphodiester α-N-acetylglucosaminidase, Golgi α-mannosidase I, N-acetylglucosaminyltransferase I, Golgi α-mannosidase II, N-acetylglucosaminyltransferase II, sialyltransferases, fucosyltransferases, galactosyltransferases, and glucosyltransferases. Also detectable are changes in glycosylation that result from a deficiency in one or more enzymes that are involved in O-linked glycosylation. These enzymes include, for example, O—N-acetylgalactosaminyltransferase, β1,3-galactosyltransferase, core 2β-N-acetylglycosaminyltransferases (see, e.g., Dennis et al. (1999) *BioEssays* 21: 412-421 for review).

In other glycosylation disorders, the defect can be in a gene that encodes an enzyme that is involved in forming a substrate for an enzyme such as a glycosyltransferase. Such accessory enzymes include, for example, those enzymes that are involved in the formation of a nucleotide sugar. The accessory enzyme can be involved in attaching the sugar to a nucleotide, or can be involved in making the sugar or the nucleotide, for example. Examples of nucleotide sugars that are used as sugar donors by glycosyltransferases include, for example, GDP-Man, UDP-Glc, UDP-Gal, UDP-GlcNAc, UDP-GalNAc, CMP-sialic acid, UDP-xylose, GDP-Fuc, GDP-GlcNAc, among others. Accessory enzymes that are involved in synthesis of nucleotide sugars are well known to those of skill in the art. For a review of bacterial polysaccharide synthesis and gene nomenclature, see, e.g., Reeves et al., *Trends Microbiol.* 4: 495-503 (1996). Accessory enzymes that might be defective and thus result in a glycosylation disorder include, for example, phosphomannomutase, phosphomannose isomerase, GDP-mannose dehydratase, GDP-mannose 3,5-epimerase, GDP-mannose 4-reductase, UDP-glucose 4' epimerase, UDP-GalNAc 4' epimerase, CMP-sialic acid synthetase, neuraminic acid aldolase, N-acetylglucosamine 2' epimerase, phosphate kinases such as pyruvate kinase, myokinase, creatine phosphate kinase, acetyl phosphate kinase, and polyphosphate kinase; and pyrophosphorylases such as UDP-Glc pyrophosphorylase, UDP-Gal pyrophosphorylase, UDP-GalNAc pyrophosphorylase, GDP-mannose pyrophosphorylase, GDP-fucose pyrophosphorylase, and UDP-GlcNAc pyrophosphorylase.

The following diseases and other conditions are examples of those that can be diagnosed using the kits and methods of the invention. However, the kits and methods of the invention are useful not only for diagnosing conditions such as those described below, but also for determining whether a glycosylation disorder is involved in a condition for which the underlying defect is not yet known. In some embodiments, the kits and methods are useful for diagnosing diseases that do not include immune system dysfunction; in other embodiments, the invention provides methods and kits that can be used to monitor immune system dysfunction.

A. Carbohydrate Deficient Glycoprotein Syndromes

One category of diseases for which the methods and kits of the invention are useful is the Carbohydrate Deficient Glycoprotein Syndromes (CDGS). FIG. 1 shows variations in E-PHA binding to glycoproteins from serum of patients having different types of CDGS. One can use the kits and methods to diagnose and/or monitor the course of treatment of not only previously known CDGS, but also to identify, diagnose, and monitor treatment of CDGS that are not yet known.

The following are representative examples the carbohydrate-deficient glycoprotein syndromes for which the kits and methods are useful.

1. CDGS Type II

In one embodiment, the invention provides diagnostic methods and kits for diagnosing CDGS Type II, which is associated with severe locomoter dysfunction, dysmorphic facial features, mental retardation, epilepsy, kyphoscoliosis, osteopenia, ventral septal defects of the heart, volvulus, obstipation, and multiple infection. This defect may also be linked to ventral septal defect (VSD), which is the leading cause of human infant mortality in the first year of life. The genetic defect responsible for CDGS Type II is in the gene that encodes GlcNAc transferase II (MGAT2) (Tan et al. (1996) *Am. J. Human Genetics* 59: 810-817).

The kits include one or more diagnostic reagents that have as their binding component the lectins E-PHA, L-PHA, or ConA. The methods involve testing blood, serum, or plasma from the human or other mammal being diagnosed for the presence of E-PHA binding. A lack of E-PHA binding to any of the samples is indicative of CDGS Type II. Similarly, an absence of L-PHA binding to blood or an increase in ConA binding to blood is also indicative of CDGS Type II.

2. CDGS Types Ia and Ib

Both of these syndromes are caused by a deficiency in mannosylation of N-linked, phospholipid, and possibly O-linked glycoconjugates. CDGS Type Ia is associated with a mutation in the PMM2 gene, which encodes phosphomannomutase. Phosphomannomutase catalyzes the conversion of Man-6-P to Man-1-P, and vice versa. Clinical features of CDGS Type Ia include hypotonia, failure to thrive, inverted nipples, unusual fat deposits, mental and psychomotor retardation, elevated liver function tests, coagulopathy, hepatomegaly, stroke-like episodes, seizures, and retinitis pigmentosa.

CDGS Type Ib results from a defect in a gene that encodes phosphomannose isomerase (PMI1), which catalyzes the interconversion of Fructose-6-P and Man-6-P. Clinical features include, for example, hypoglycemia, protein losing enteropathy, failure to thrive, vomiting, diarrhea, and congenital hepatic fibrosis.

The CDGS Type Ia and Ib glycosylation disorders generally result in a quantitative change in binding of a detection reagent, rather than an elimination of binding. For example, a particular protein might normally have three attached oligosaccharides, but in a CDGS Type Ia or Ib sample might have 0, 1, or 2 attached oligosaccharides. Accordingly, one will preferably use a diagnostic reagent that is capable of quantitating the number of attached oligosaccharides. One example of a suitable diagnostic reagent is ConA.

More preferably, an antibody is used as the diagnostic reagent. The elimination of one or more oligosaccharides from a particular glycoprotein would be expected to change the conformation of the glycoprotein. Accordingly, one can immunize an animal with a purified protein (e.g., transferrin) from a CDGS patient and screen for binding only to the defective transferrin.

3. CDGS Type III and Type V

Clinical features of CDGS Type III include perinatal floppiness without polyneuropathy or cerebellar hypoplasia. Generalized dysmyelination is also observed. Type V has recently been identified.

The particular genetic defect that is responsible for CDGS Type III is as yet unknown. Accordingly, the invention provides methods of identifying diagnostic reagents suitable for diagnosing CDGS Type III. The methods involve screening various samples from CDGS Type III patients with a panel of potential binding components such as those listed in Table 1. Those binding components for which a difference in binding is observed for samples from CDGS Type III patients compared to samples from normal patients are then used to diagnose CDGS Type III.

4. CDGS Type IV

CDGS Type IV clinical indications include essentially no psychomotor development, reduced responsiveness, severe epileptic seizures, hypotonia, gothic palate, microcephaly, and optic atrophy. The genetic defect causes a disruption in dolicol phosphate mannose synthase. Diagnostic reagents include ConA, E-PHA, as well as specific antibodies.

B. Core 2 GlcNAc Transferase Deficiency

The Core 2 GlcNAc transferase (C2 GlcNAc-T) controls the production of a class of O-linked oligosaccharide structures in mammals, including mouse and man. Prior to the present invention, C2 GlcNAc-T deficiency had never been diagnosed because of the lack of C2 GlcNAc-T-specific reagents and knowledge of C2 GlcNAc-T function. The absence of C2 GlcNAc-T in mice was found to result in a myeloid insufficiency and reduced inflammation responses (see, Example 2). These reduced physiologic responses to chemicals and pathogens create an opportunistic environment for disease initiation and progression.

Figure 5:
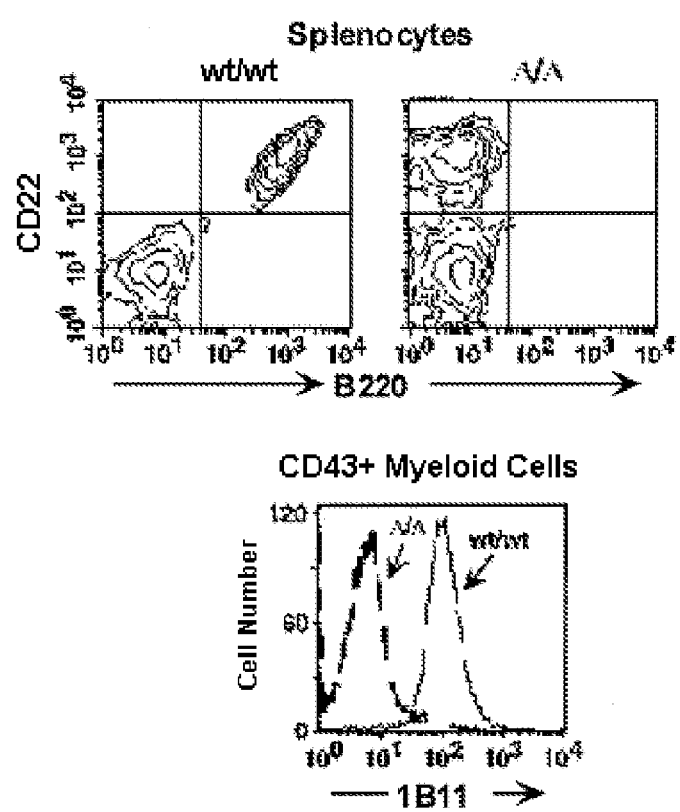
FIG. 5 shows the results of an experiment in which the antibodies B220 and 1B11 were used to diagnose a deficiency in the inflammatory response that results from a deficiency in Core 2 GlcNAc transferase activity.

The present invention provides kits and methods for diagnosing C2 GlcNAc-T deficiency in humans and other mammals. The kits include the either or both of the antibodies B220 and 1B11, which specifically recognize Core 2 type glycans. C2 GlcNAc-T deficiency is diagnosed by a loss of B220 and/or 1B11 binding to a blood sample from the human or other mammal being tested (FIG. 5).

C. Congenital Dyserythropoietic Anemias

The Congenital Dyserythropoietic Anemias (CDAs) are a group of inherited diseases of previously unknown etiologies. The severity of the conditions is varied. CDA Type II (also known as HEMPAS) is an autosomal recessive disease associated with a deficit in glycosylation involving the erythrocyte Band 3 protein. A partial indicator of this disease is low levels of α-mannosidase-II (αM-II). CDA Type II patients exhibit mild to moderate anemia, and variable symptoms can include jaundice, cirrhosis of the liver, diabetes, and gallstones.

Figure 6:
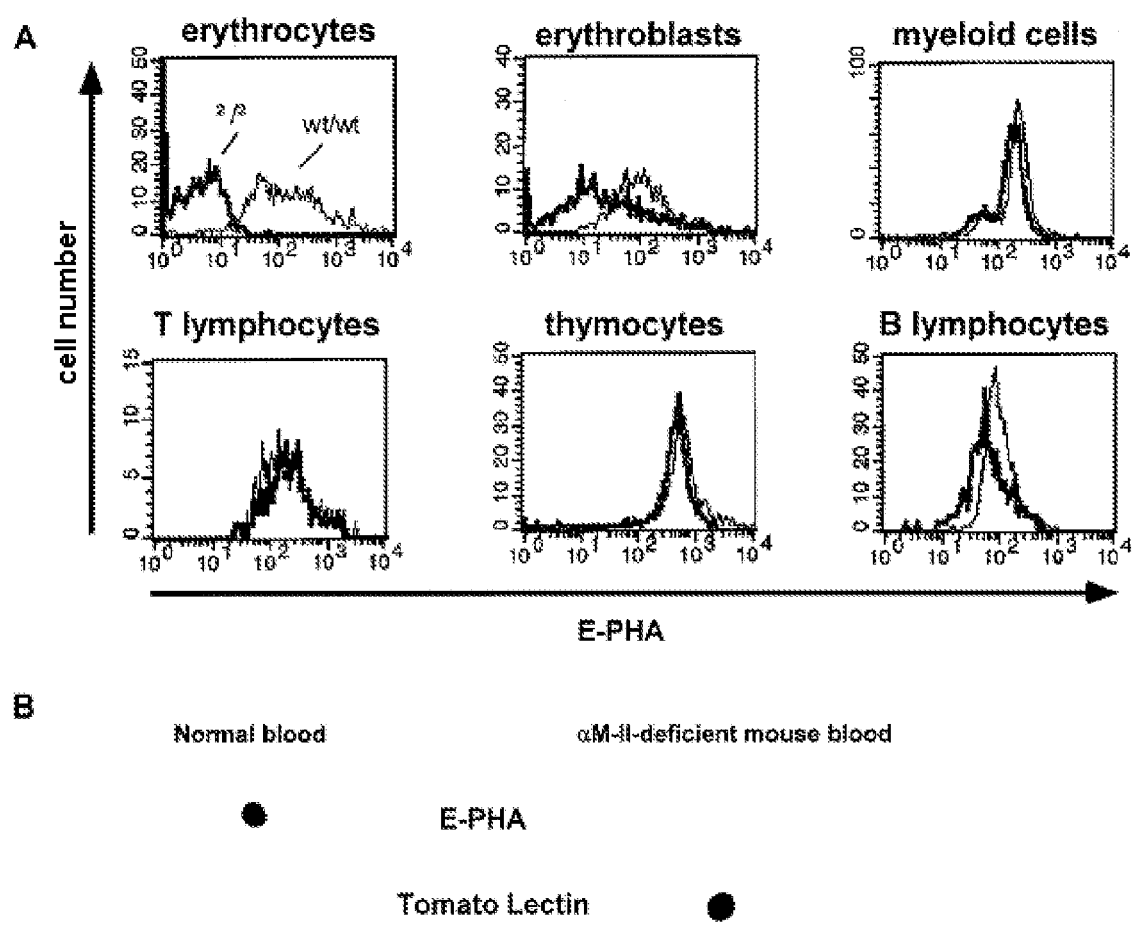
FIG. 6 shows the results of an experiment in which CDA Type II/HEMPAS was diagnosed by detecting a loss in E-PHA binding.

The present invention provides methods and kits for diagnosing CDA Type II/HEMPAS. The diagnostic reagents used in the kits and methods can include E-PHA, for which is observed a significant reduction in binding to blood from humans or other animals that are deficient in αM-II activity (FIG. 6). Another useful diagnostic reagent is tomato lectin, which does not bind to blood from αM-II-deficient mammals.

Whole blood is a preferred sample for diagnosing this condition, as the deficiency in glycosylation only affects erythroid cells. All other cell types studied use an alternate pathway that does not involve αM-II.

D. Leukocyte Adhesion Deficiency II

Leukocyte Adhesion Deficiency II (LAD II) is associated with a defect in mobilization of fucose. Many proteins are hypofucosylated. Human serum contains several core-fucosylated glycoproteins, but the most prominent is the µ-chain of immunoglobulin IgM. LADII patients are predicted to be deficient in core fucosylation of this and other serum proteins. The monoclonal antibody CAB4 is an example of an effective diagnostic reagent for diagnosing LAD II (Example 6 and FIG. 7).

E. Immune System Disorders

The present invention also provides methods and kits for diagnosing and monitoring immunodeficiencies. The immune deficiencies can result from a genetic defect, or can arise from other factors that result in a glycosylation disorder. Numerous immunodeficient states exist in humans, and a significant number are of unknown etiology. Prior to the present invention, no screens were available by which one could screen these immunodeficient states for potential association with a glycosylation disorder.

The methods of the invention involve detecting the levels of α2,3 sialylgalactosides (to monitor CTL immune system function) and α2,6 sialylgalactosides (to monitor humoral immune system function) in a sample from a patient.

1. B Lymphocyte-Mediated Immunodeficiency

B lymphocyte-mediated immunodeficiency is associated with a decrease in the levels of α2,6 sialylgalactosides. The α2,6-sialyltransferase ST6Gal is essential for producing an oligosaccharide terminus (Sia6LacNAc) that is recognized by the mammalian B cell lectin CD22.

The physiological relevance of ST6Gal I was unknown until knockout mice were obtained as described in Example 4. Autosomal recessive lesions of ST6Gal resulted in an immunodeficient state with reduced efficacy of B lymphocyte immune activation and reduced antibody formation. A decrease in the amount of Siaα2-6Galβ1-4GlcNAc (Sia6LacNAc) trisaccharide in a sample is associated with a marked immunodeficiency characterized by a deficit in B cell activation.

Figure 3:
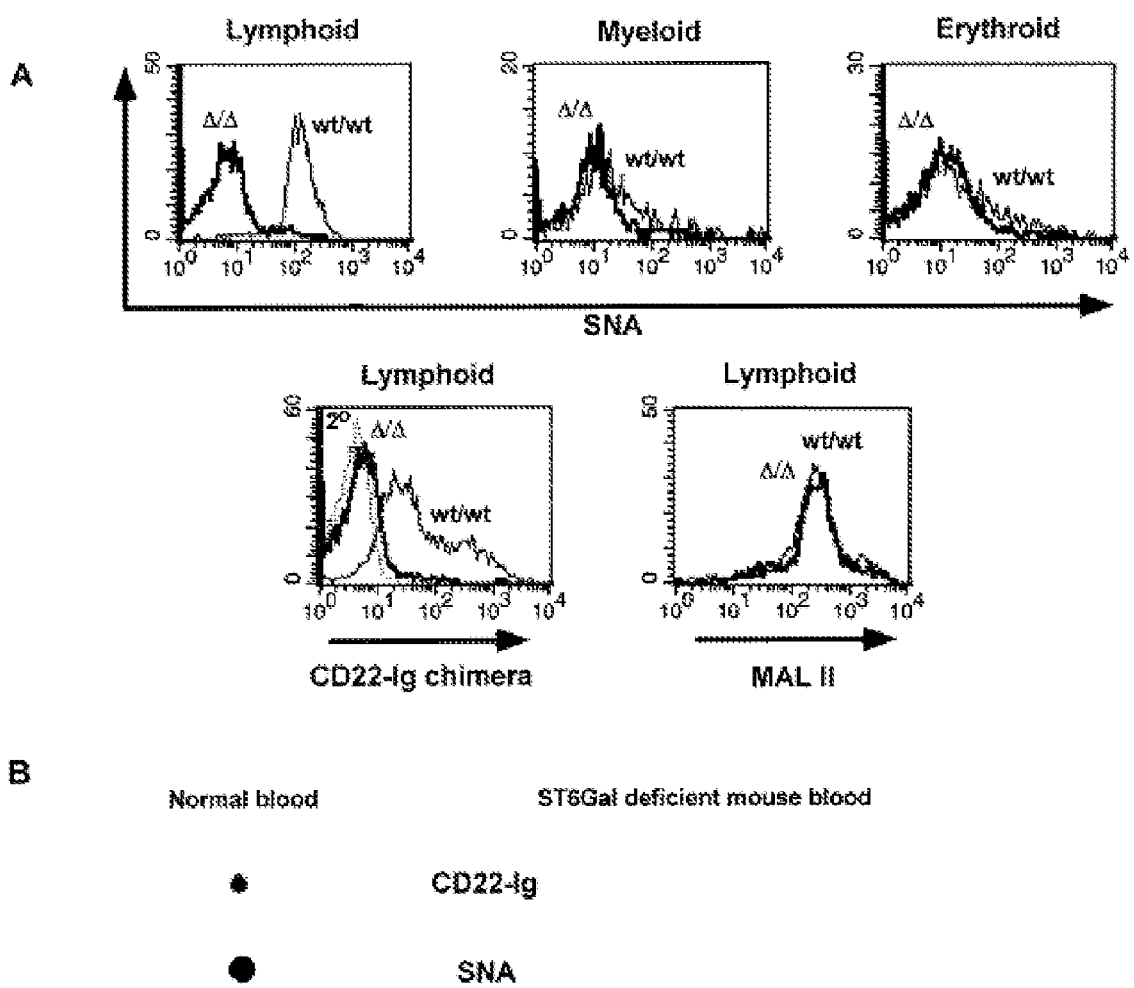
FIG. 3 shows the results of an experiment in which CD22-Ig and SNA were used to diagnose a deficiency in B cell immune responses associated with a reduction of ST6Gal sialyltransferase activity.

The methods and kits of the invention employ either or both of an SNA lectin and a CD22 lectin (the latter preferably attached to an immunoglobulin molecule) (FIG. 3). The lectin *Sambucus nigra* bark agglutinin (SNA), which can be isolated from the inner bark (bast tissue) of elder stems and branches or obtained commercially (Sigma Chemical Co., St. Louis Mo.), has an affinity for NeuNAc-α2-6-Gal, NeuNAc-α2-6-GalNAc, and, to a lesser extent, NeuNAc-[2-3]-Gal (Shibuya et al. (1987) *J. Biol. Chem.* 262: 1596). CD22 or a moiety having the Sia6LacNAc binding activity of CD22 can also be used to detect the presence or absence of Sia6LacNAc. Commercially available detection reagents that are suitable for use in diagnosing this type of immunodeficiency according to the methods of the invention include SNA-fluorescein isothiocyanate (FITC) lectin (FL-1301, Vector Laboratories, Burlingame Calif.) and biotinylated SNA lectin (B-1305, Vector Laboratories).

Samples that can be tested using these diagnostic reagents include, for example, whole blood and various other tissues.

2. CTL-Mediated Immunodeficiency

A decrease in the amount of α2,3-sialylgalactosides in a sample is associated with another type of immunodeficiency which is characterized by a decrease in cytotoxic T cell abundance and activity (see, Example 5). The sialyltransferase ST3Gal I acts at the termini of Core 1 type O-linked oligosaccharides to create the structure Siaα2-3Galβ1-3GalNAc.

Figure 4:
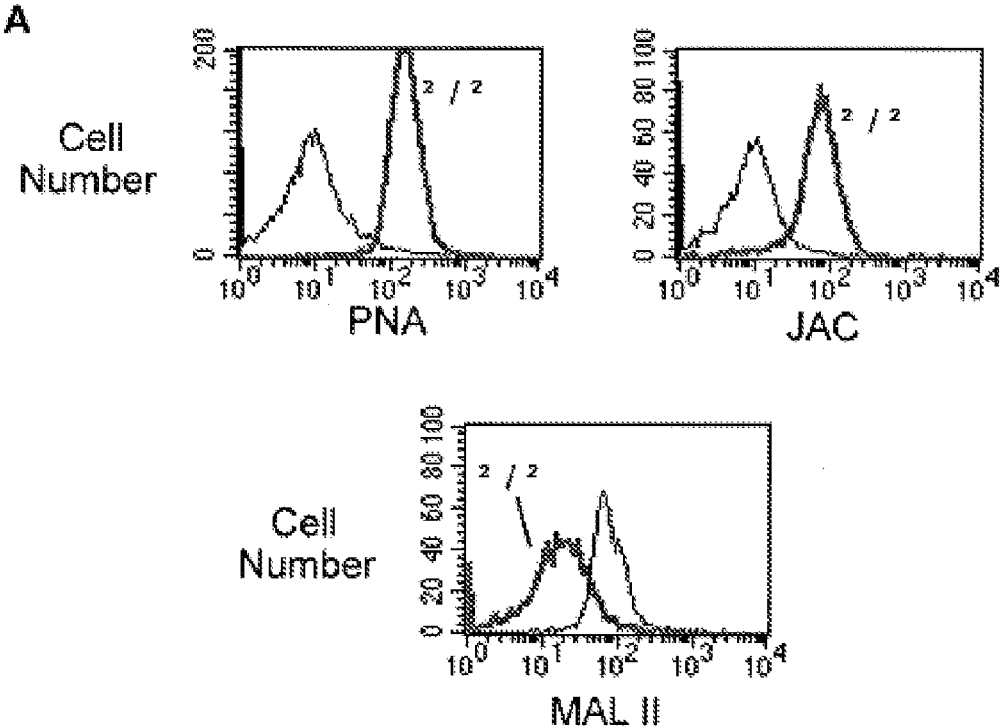
FIG. 4 shows the results of an experiment in which the lectins PNA, JAC, and MAL-II were used to diagnose T cell-mediated immunodeficiency in which the activity of a ST3Gal I sialyltransferase is reduced or eliminated.
Figure 4:
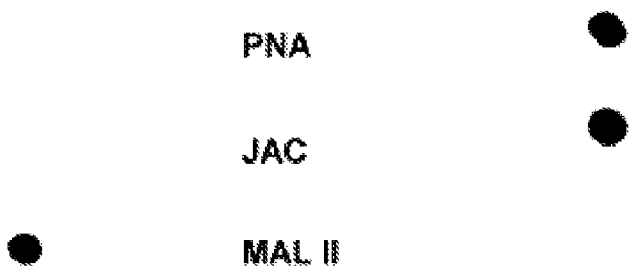

The methods and kits of the invention can use a diagnostic reagent based on the lectin peanut agglutinin (PNA), which binds to Galβ1-3GalNAc but does not bind to Siaα2-3Galβ1-3GalNAc (FIG. 4). Jacalin (JAC) has a similar specificity. Accordingly, one can diagnose a deficiency in ST3Gal I is by observing an increase in binding of either of these two reagents to a sample. Suitable test samples include blood and a variety of other tissues.

Another example of a suitable binding agent for this condition is the MAL II lectin, which can be isolated from *Maackia amurensis* seeds. MAL II binds to sialic acids in an α2,3 linkage. Thus, in contrast to PNA and JAC, a deficiency in ST3Gal I is diagnosed by observing a decrease in MAL II binding. Commercially available detection reagents that are useful for diagnosing this condition include, for example, MAL II-FITC lectin and biotinylated MAL II lectin (B-1265, Vector Laboratories).

Other Conditions Associated with Glycosylation Disorders

Many other conditions are known to be, or suspected to be, associated with glycosylation disorders. Among these are autoimmune syndromes, such as systemic autoimmune disease, including glomerulonephritis (kidney), which can be diagnosed according to the methods of the invention by using E-PHA: deficiency in profile. For example, one can run proteins on a gel, blot, and detect with E-PHA. A loss of E-PHA binding to red blood cells is also indicative of this disorder. SLE and arthritis are additional diseases potentially or actually associated with glycosylation disorders. For example, arthritis diagnosis can involve the use of a diagnostic reagent that binds to galactosylated oligosaccharides. Autoimmunity can be diagnosed by changes in reactivity to lectins, including: E-PHA, SNA, MALII, and the like.

Other conditions potentially associated with glycosylation disorders include generalized failure to thrive, "funny looking kid" syndrome, autism, other conditions where pediatric care is unsuccessful. Other defects include generalize immune suppression, defects in inflammation, mental retardation, protein losing enteropathy (a symptom of CDGS Type I).

Transgenic Animal Model Systems for Studying Glycosylation Disorders

The invention also provides chimeric and transgenic non-human animals that contain cells that lack at least one gene that is functional in wild-type cells of the animal and is involved in glycosylating proteins, lipids, proteoglycans, and the like. Methods for producing such animals are also provided.

The chimeric and transgenic animals of the invention are useful as model systems for studying glycosylation disorders and for developing methods for diagnosing and treating these disorders. The chimeric and transgenic animals of the invention are also useful for several other purposes, including the study of the mechanisms by which glycosylation influences immune responses, CDGS, and other effects. Samples obtained from the animals can be used to develop diagnostic methods for detecting these conditions. "Knockout" animals of the invention can also be used for producing glycoproteins and glycolipids that, when produced in a wild-type animal, would carry a saccharide residue that is not desirable for a particular application.

Of particular interest for studying and diagnosing B lymphocyte- and CTL-mediated immunodeficiencies are chimeric and transgenic animals that lack either an ST6Gal sialyltransferase gene or an ST3GalI sialyltransferase gene, respectively. Similarly, chimeric and transgenic animals that are defective in phosphomannomutase (PMM2), phosphomannose isomerase (PMI1) are useful for studying and developing diagnostic methods for CDGS Type Ia and Type Ib, respectively. Chimeric and transgenic animals that lack GalNAc transferase II (MGA T2) can be used to study and develop diagnostic methods for CDGS Type IIa. Core 2 GlcNAc transferase-deficient chimeric and transgenic animals are useful for the study of the initiation and progression of inflammation, as well as for developing methods for diagnosing defects in the inflammatory process. Chimeric and transgenic animals that lack a fucosyltransferase gene are useful for the study and diagnosis of Leukocyte Adhesion Deficiency II. Indeed, a transgenic or chimeric animal that is defective for any glycosyltransferase gene, or for other genes that are involved in glycosylation (e.g., genes that encode an enzyme that is involved in synthesis of a nucleotide sugar which acts as a donor for a glycosyltransferase) find use.

Other transgenic and chimeric animals of interest are those in which other genes that encode enzymes involved in glycosylation are defective. Of particular interest are animals having a defect in one or more genes that encode oligosaccharyltransferase, α-glucosidase I, α-glucosidase II, ER α1,2-mannosidase, N-acetylglucosaminyl-phosphotransferase, N-acetylglucosamine-1-phosphodiester α-N-acetylglucosaminidase, Golgi α-mannosidase I, N-acetylglucosaminyltransferase I, Golgi α-mannosidase II, N-acetylglucosaminyltransferase II, a fucosyltransferase, a galactosyltransferase, and a glucosyltransferase, as well as genes that encode enzymes involved in O-linked oligosaccharide synthesis.

A "chimeric animal" includes some cells that lack the functional gene of interest and other cells that do not have the inactivated gene. A "transgenic animal," in contrast, is made up of cells that have all incorporated the specific modification which renders the particular gene inactive. While a transgenic animal is capable of transmitting the inactivated gene to its progeny, the ability of a chimeric animal to transmit the mutation depends upon whether the inactivated gene is present in the animal's germ cells.

The modifications that inactivate the gene of interest can include, for example, insertions, deletions, or substitutions of one or more nucleotides. The modifications can interfere with transcription of the gene itself, with translation and/or stability of the resulting mRNA, or can cause the gene to encode an inactive polypeptide. For example, the gene of interest can be completely or partially deleted in the chimeric and transgenic animals of the invention, or can be inactivated due to a mutation in the coding sequence or control sequence that prevents the gene from encoding an active enzyme. A mutation in a promoter region can prevent expression of the gene; a mutation at an intron splice site, for example, can prevent proper processing of an mRNA. A mutation in the coding region can, for example, result in a nonsense mutation that results in premature termination of the encoded polypeptide, or can result in a frameshift or missense mutation that results in the encoding of a polypeptide that lacks the enzymatic activity.

The methods of the invention are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, Calif., Ed., *Transgenic Animal Technology: A Laboratory Handbook*, Academic Press, 1994.

One method of obtaining a transgenic or chimeric animal having an inactivated glycosylation-associated gene in its genome is to contact fertilized oocytes with a vector that includes a polynucleotide which encodes the enzyme of interest, but is modified to contain an inactivating modification. For some animals, such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoel cavity, typically at the 64 cell stage. If desired, the presence of a desired inactivated gene in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C.S.H.L. N.Y. (1986) (mouse embryo); Hammer et al. (1985) *Nature* 315: 680 (rabbit and porcine embryos); Gandolfi et al. (1987) *J. Reprod. Fert.* 81: 23-28; Rexroad et al. (1988) *J. Anim. Sci.* 66: 947-953 (ovine embryos) and Eyestone et al. (1989) *J. Reprod. Fert.* 85: 715-720; Camous et al. (1984) *J. Reprod. Fert.* 72: 779-785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the modified glycosylation-associated gene can be introduced into embryonic stem cells (ES). These cells are obtained from preimplantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255-258. Transformed ES cells are combined with blastocysts from a nonhuman animal. The ES cells colonize the embryo and in some embryos form the germ line of the resulting chimeric animal. See, Jaenisch, *Science,* 240: 1468-1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810-813.

The introduction of the modified glycosylation-associated gene into recipient cells can be accomplished by methods known to those of skill in the art. For example, the modified gene can be targeted to the wild type locus by homologous recombination. Alternatively, a recombinase system can be employed to delete all or a portion of a locus of interest. Examples of recombinase systems include, the cre/lox system of bacteriophage P1 (see, e.g., Gu et al. (1994) *Science* 265: 103-106; Terry et al. (1997) *Transgenic Res.* 6: 349-356) and the FLP/FRT site specific integration system (see, e.g., Dymecki (1996) *Proc. Nat'l. Acad. Sci. USA* 93: 6191-6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the sialyltransferase gene of interest. See, e.g., Tsien et al. (1996) *Cell* 87: 1317-26; Brocard et al. (1996) *Proc. Nat'l. Acad. Sci. USA* 93: 10887-10890; Wang et al. (1996) *Proc. Nat'l. Acad. Sci. USA* 93: 3932-6; Meyers et al. (1998) *Nat. Genet.* 18: 136-41).

EXAMPLES

The following examples are offered to illustrate, but not to limit the claimed invention.

Materials and Methods

The following materials and methods were used in the examples described herein, except where otherwise noted.

Cytometry

Blood samples are obtained and incubated with commercially available lectins or antibodies that are conjugated with reagents for detection, such as biotin. Incubation with lectins (concentrations of a few ng/ml to a few µg/ml) is done at room temperature or on ice for 30 minutes in physiologic saline (with $Ca^{2+}$ and $Mg^{2+}$ as necessary) buffered to pH 7. Cells are washed and detection system (such as streptavidin-FITC) is applied for brief period, e.g., 15 minutes. Cells are then analyzed by flow cytometry.

Dot Blots

Blood, plasma or serum samples are obtained and protein concentrations determined using Bradford or Lowry method. Equivalent protein levels are dotted onto nitrocellulose and air dried for 30 minutes. Blots are incubated with lectins at specific concentrations (a few ng/ml to a few µg/ml) and then are washed briefly. Secondary detection reagent (e.g., goat anti-biotin-horseradish peroxidase) is applied for 30 minutes followed by a wash. Detection is by chemiluminesence (ECL) and developed on film for 3 minutes. However, calorimetric detection systems work as well and are equally rapid.

Example 1

Diagnosis of Carbohydrate Deficient Glycoprotein Syndrome Type II

Carbohydrate Deficient Glycoprotein Syndrome (CDGS) Type II is an autosomal recessive disease that was first discovered in a test for alcoholism. Two patients have been reported since the syndrome was first molecularly defined as two separate point mutations in the MGAT2 gene, which encodes GlcNAc transferase II. The disease is characterized by severe locomotor dysfunction, dysmorphic facial features, mental retardation, epilepsy, kyphoscoliosis, osteopenia, ventral septal defects of the heart, volvulus and obstipation, as well as multiple infections.

A knockout mouse model was made in which the MGAT2 gene is defective. Most homozygotes died within the first week after birth. Survivors were obtained that exhibited phenotypes that match the human disorder. Plasma, blood, and serum from the knockout mouse was tested to identify potential diagnostic reagents. The lectin E-PHA was found to bind to blood, plasma, and serum from normal mice, but not to the corresponding samples from the MGA T2-null mice. A difference in binding was also observed for blood tested with the lectin L-PHA, which did not bind to blood from the knockout mice, but did bind to blood from normal mice. Conversely, the ConA lectin exhibited increased binding to blood from the knockout mice compared to binding to blood from normal mice.

Figure 2:
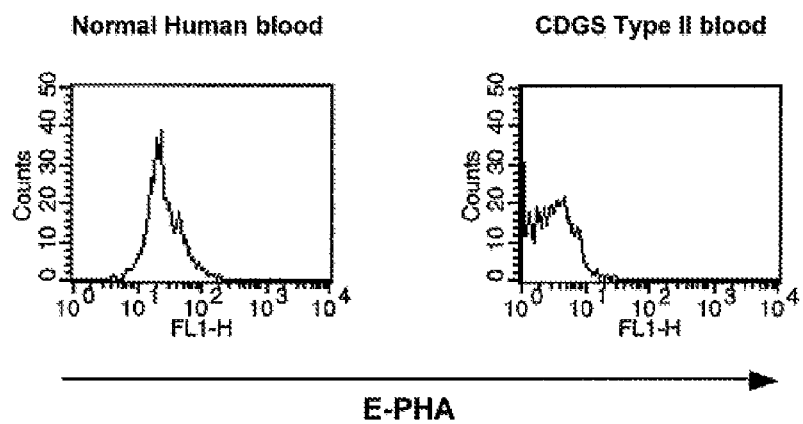
FIG. 2 shows the results of an experiment in which the lectin E-PHA was used to diagnose CDGS Type II.
Figure 2:

These diagnostic reagents were then tested against the corresponding samples from normal and CDGS Type II human patients (FIG. 2). Blood from the CDGS Type II human patient was devoid of E-PHA lectin binding, as shown in FIG. 2, as was plasma and serum. Blood from the CDGS Type II human patient was also devoid of L-PHA lectin binding and exhibited increased binding to ConA lectin.

Example 2

Diagnosis of Core 2 GlcNAc Transferase Deficiency

Figure 8:
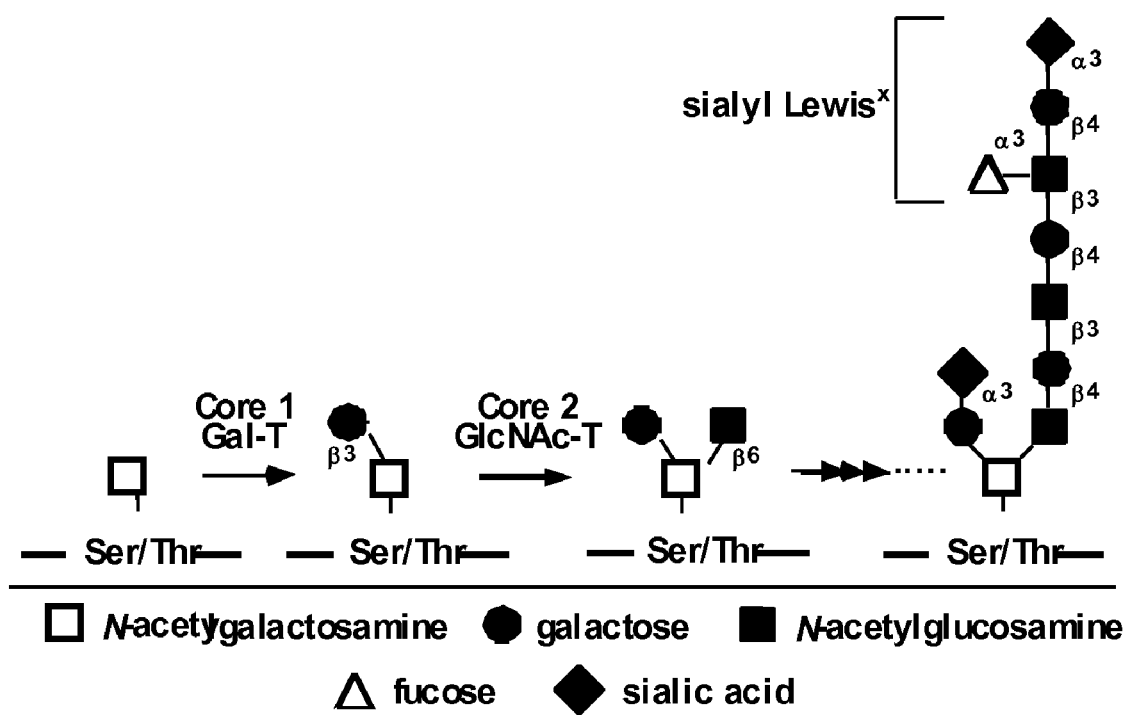
FIG. 8 shows a diagram of mammalian O-glycan biosynthesis, specifically the production of Core 1 and Core 2 O-glycans. The core 2 GlcNAcT enzyme functions in generating bi-antennary O-glycans in the Golgi. The core 2 branch provides a scaffold for the subsequent production of lactosamine disaccharide repeats and the selectin ligand sialyl Lewis X.

This Example describes the development of a diagnostic method for detecting Core 2 GlcNAc transferase deficiency. The Golgi enzyme core 2 β-1,6-N-acetylglucosaminyltransferase (C2 GlcNAcT) is generally involved in the synthesis of mammalian serine/threonine-linked oligosaccharides (O-glycans) (FIG. 8). Core 2 O-glycans have been hypothesized to be essential for mucin production and selectin ligand biosynthesis.

This Example demonstrates that mice lacking C2 GlcNAcT exhibit a restricted phenotype with neutrophilia and a partial deficiency of selectin ligands. Loss of core 2 oligosaccharides reduces neutrophil rolling on substrata bearing E-, L- and P-selectins and neutrophil recruitment to sites of inflammation. However, the diminished presence of L-selectin ligands on lymph node high endothelial venules does not affect lymphocyte homing. These studies indicate that core 2 oligosaccharide biosynthesis segregates the physiologic roles of selectins and reveal a function for the C2 GlcNAcT in myeloid homeostasis and inflammation.

A C2 GlcNAc-T-deficient transgenic mouse was constructed and used to study the effects of C2 GlcNAc-T deficiency, and also to develop an assay for diagnosing such deficiency. The assay is useful for detecting the state of a human or other animal's ability to mount an inflammatory response.

Experimental Procedures

A. Gene Targeting of the C2 GlcNAcT and Production of Mutant Mice

Isolation of mouse C2 GlcNAcT genomic DNA and construction of a targeting vector bearing Cre loxP recombination signals was accomplished similarly as described (Priatel et al. (1997) *Glycobiology* 7: 45-56). RI ES cells (Nagy et al. (1993) *Proc. Nat'l. Acad. Sci. USA* 90: 8424-8428) were electroporated with 10 µg of the linearized targeting construct and the resulting clones were screened by Southern blotting using the genomic probe. Targeted ES cells were electroporated with 5 µg of Cre expression plasmid and subclones bearing the C2 GlcNAcT$^\Delta$ and C2 GlcNAcT$^F$ alleles were isolated. C2 GlcNAcT$^\Delta$ and C2 GlcNAcT$^F$ chimeric mice were generated using standard techniques (Metzler et al. (1994) *EMBO J.* 13: 2056-2065) and were crossed into the C57BL/6 background for the generation of heterozygous and homozygous offspring. C2 GlcNAcT alleleic structure was analyzed by Southern blotting and PCR. The wild type C2 GlcNAcT allele was detected using PCR primers adjacent to the deleted region (W5': 5'-GGG TTA CGG ATG AGC TCT GTG TC-3' (SEQ ID NO: 1) and W3': 5'-CCC TGG AAG CAG GAC AAT TCT G-3' (SEQ ID NO:2)) resulting in a 304 bp fragment, while the mutant allele was detected using W5' and a loxP primer (M3': 5'-CTC GAA TTG ATC CCC GGG TAC-3' (SEQ ID NO:3)), yielding a 200 bp fragment.

B. C2 GlcNAcT Enzyme Assays and Oligosaccharide Analysis

The enzyme assay mixture containing 50 mM Mes (pH 7.0), 0.5 µCi of UDP-[$^3$H]GlcNAc in 1 mM UDP-GlcNAc, 0.1 M GlcNAc, 10 mM EDTA, 1 mM acceptor and 25 µl cell lysate from normal, heterozygous or homozygous null tissues in a total volume of 50 µl was incubated at 37° C. for 1 h followed by C18 Sep-Pak (Waters) processing (Bierhuizen and Fukuda (1992) *Proc. Nat'l. Acad. Sci. USA* 89: 9326-9330; Yousefi et al. (1991) *J. Biol. Chem.* 266: 1772-1782). For oligosaccharide analyses, splenocytes from wild type or C2 GlcNAcT null animals were metabolically labeled with [$^3$H]glucosamine (10 µCi/ml) for 24 h and processed according to described procedures (Bierhuizen et al. (1994) *J. Biol. Chem.* 269: 4473-4479; Maemura and Fukuda (1992) *J. Biol. Chem.* 267: 24379-24386). O-Linked oligosaccharides were initially analyzed by Bio-Gel P-4 gel filtration as previously reported (Maemura and Fukuda (1992), supra.). Sialylated O-glycans were then desialylated and analyzed by HPLC using an amino-bonded column and standard techniques (Piller et al. (1988) *J. Exp. Med.* 173: 1501-1510.

C. Flow Cytometry

Single cell suspensions of splenocytes were prepared and erythrocytes removed by ammonium chloride lysis. Cells were incubated in the presence of antibodies (below) in FACS buffer (2% FCS in PBS) for 20 minutes at 4° C. For E- or P-selectin binding, cells were treated with 0.5 µg/ml of Fc Block (anti-CD32/16, PharMingen), then incubated with Gr-1 and either the E- or P-selectin-IgM chimera (Maly et al. (1996) *Cell* 86: 643-653) with or without addition of 5 mm EDTA for 30 minutes at 4° C. Cells were washed and incubated with a goat anti-human FITC conjugated secondary antibody (Sigma) as appropriate. Antibodies used were CD11a (M17/4), CD11b (M1/70), CD18 (C71/16), CD22 (Cy34.1), CD24 (M1/69), CD43 (S7 and 1B11), CD45 (30-F11), CD45R/B220 (RA3-6B2), CD62L (MEL-14), and Gr-1 (RB6-8C5) (PharMingen). The anti-PSGL-1 antibody, 4RA10 was a generous gift from Dr. D. Vestweber. Data were analyzed on a FACScan flow cytometer using CELLQUEST™ software (Becton Dickinson).

D. Hematology

Blood from the tail vein of methoxyfluorane anethetized mice was collected into EDTA-coated polypropylene microtubes (Becton Dickinson). Analyses of red blood cells, white blood cells and platelet cell numbers and morphology were carried out manually and with a CELL-DYN 3500 calibrated with normal mouse blood (UCSD Medical Center, Hillcrest).

E. Bone Marrow Progenitor Assay

Bone marrow was flushed from the femurs of wild type or C2 GlcNAcT null mice with 2% FBS in PBS and single cell suspensions prepared by aspirating gently through a 25 g needle. $1.5 \times 10^4$ nucleated cells were plated into 35 mm dishes in triplicate in Methocult M3434 (Stemcell Technologies Inc.). Dishes were incubated at 37° C., 5% $CO_2$ for 10-12 days and colonies enumerated using light microscopy.

F. Leukocyte Rolling

Soluble murine E-, P- and L-selectin IgG chimeric molecules were coated onto polystyrene dishes and assembled in a parallel plate flow chamber (GlycoTech, Rockville, Md.). Neutrophils from wild type, C2 GlcNAcT$^{\Delta/\Delta}$ or FucT-VII$^{-/-}$ mice were prepared at a concentration of $1 \times 10^6$/ml in rolling medium, 0.2% BSA in HBSS without calcium and magnesium (Life Technologies, Inc., Gaithersburg, Md.) supplemented with 10 mM HEPES, pH 7.2. The calcium concentration was adjusted to 2 mM immediately prior to infusion of the neutrophils into the flow chamber for 30 seconds at 5 dyn/cm$^2$ using a syringe pump (KD Scientific Inc., Boston, Mass.). This infusion was stopped for 3 min to allow for static adhesion of the neutrophils to the substrate and then restarted at 0. 19 dyn/cm$^2$ Wall shear forces were doubled every two minutes without interrupting the cell flow. Fields of neutrophils were observed using a 10× objective, and the scene was recorded on VCR tape. Image analysis was performed on 6100/66 Power Macintosh using the Scion version of the public domain NIH Image program (Scion Corporation, Frederick, Md.). The fraction of cells remaining adherent under static conditions after 2 minutes at each specific shear force was determined by manually enumerating the cells and dividing this number by the number of adherent cells observed immediately preceding the initiation of flow (i.e., 100% represents cells found in the observed field after static adhesion, prior to initiation of the lowest shear flow rate).

G. Peritoneal Inflammation

Mice were injected intraperitoneally with 1 ml of 3% thioglycollate (Sigma). At the indicated times, mice were sacrificed and the peritoneal cavities lavaged with 10 ml of ice cold PBS containing 1% BSA and 0.5 mM EDTA. Red blood cells were removed by hypotonic lysis and leukocytes counted manually using a hemocytometer. Cytospins were stained with Leukostat (Sigma) and neutrophils counted. Peritoneal exudates were also stained with Gr-1 and F4/80 (Caltag) and analyzed by flow cytometry.

H. Lymphocyte Trafficking

To determine the cellularity of secondary lymphoid organs, tissues were dissected from wild type and C2 GlcNAcT homozygous null mice. Single cell suspensions of lymphocytes from mesenteric lymph nodes, peripheral (axillary and brachial) lymph nodes and Peyer's patches were enumerated manually using a hemocytometer. Frozen sections of axillary and brachial lymph nodes were cut at 5 μm, air dried and fixed in acetone prior to staining with hematoxylin and eosin. In separate experiments, an L-selectin-IgM was applied to frozen sections of peripheral lymph nodes as previously described (Maly et al. (1996) supra.; Smith et al. (1996) *J.* *Biol. Chem.* 271: 8250-8259). Serial sections were stained with the peripheral node addressin antibody, MECA 79. Lymphocyte homing assays were carried out as previously described (Maly et al. (1996), supra. Briefly, $2.5 \times 10^7$ CMFDA (Molecular Bioprobes) labeled wild type mesenteric leukocytes were injected into the tail vein of wild type or C2 GlcNAcT$^{\Delta/\Delta}$ mice. After 1 h, the animals were sacrificed and hematopoietic organs removed. Analysis of 100,000 CMFDA positive leukocytes was carried out by flow cytometry.

I. Statistical Analysis

Data were analyzed by Student's t test for unpaired samples using StatView® software.

Results

A. Targeted Mutagenesis and Deletion of the C2 GlcNAcT Gene

Figure 9:
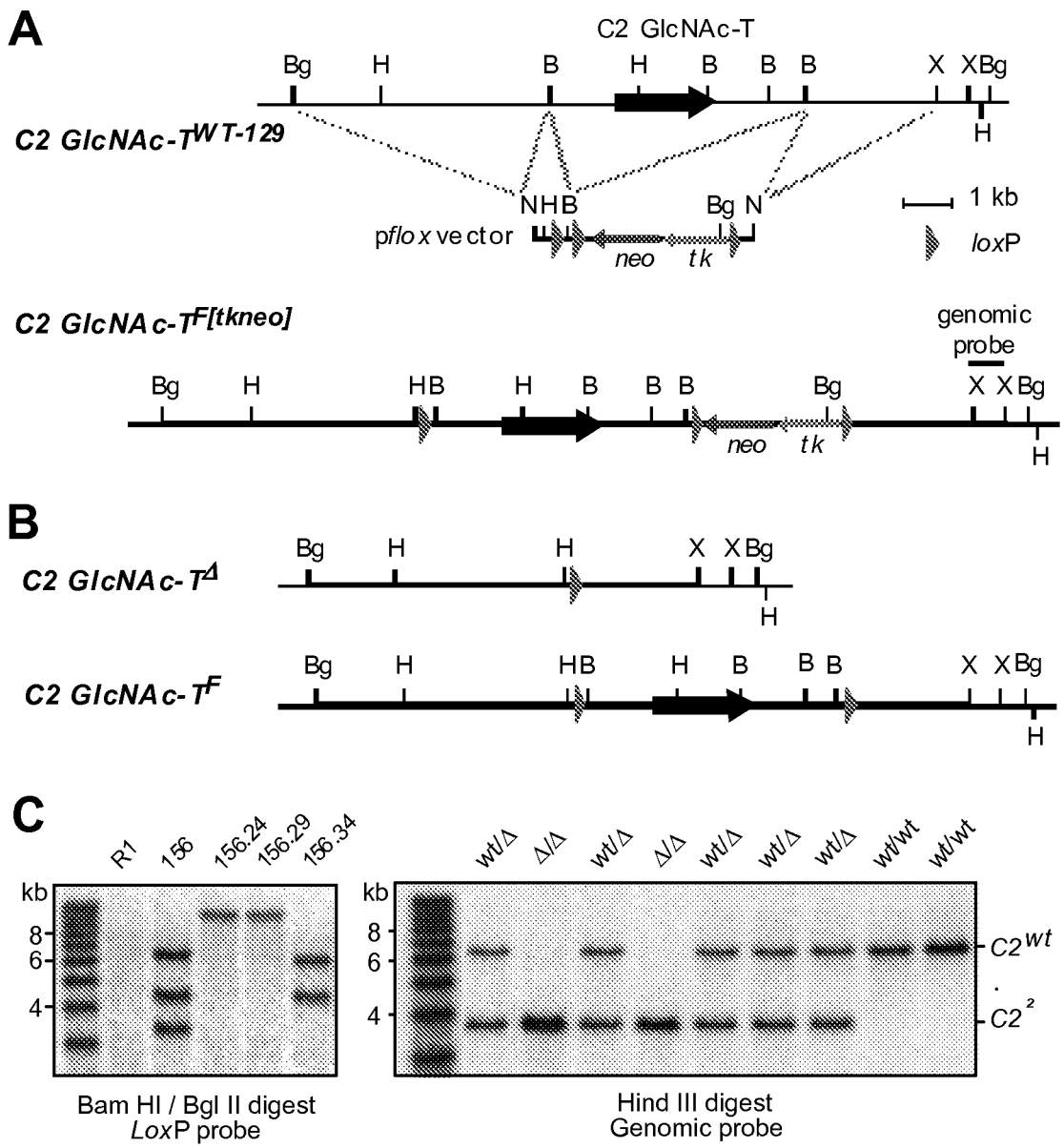
FIG. 9A-FIG. 9C show the strategy used for deletion of the C2GlcNAcT gene in embryonic stem cells and mice.

C2 GlcNAcT is a Golgi localized type II transmembrane glycosyltransferase and is conserved among mammals studied (Bierhuizen and Fukuda (1992) *J. Biol. Chem.* 89: 9326-9330; Sekine et al. (1997) *J. Biol. Chem.* 272: 27246-27252). A mouse genomic clone encompassing the single C2 GlcNAcT protein-coding exon was used in constructing a gene-targeting vector designed to control exon deletion by Cre-loxP recombination (FIG. 9A). Homologous recombination of the targeting vector in embryonic stem (ES) cells incorporated selection markers and 3 loxP sites for the subsequent production of systemic C2 GlcNAcT$^{\Delta}$ or conditional C2 GlcNAcT$^F$ mutations in vivo (FIG. 9B and FIG. 9C). These alleles were transmitted into the mouse germline and offspring homozygous for either the C2 GlcNAcT$^{\Delta}$ or C2 GlcNAcT$^F$ allele were generated. Such offspring were present among 25% of littermates, lacked overt physical or behavioral abnormalities, developed normally and were fully fertile. Mice homozygous for C2 GlcNAcT$^{\Delta}$ allele were further analyzed.

B. C2 GlcNAcT Activity and Core 2 O-Glycan Abundance

Figure 10:
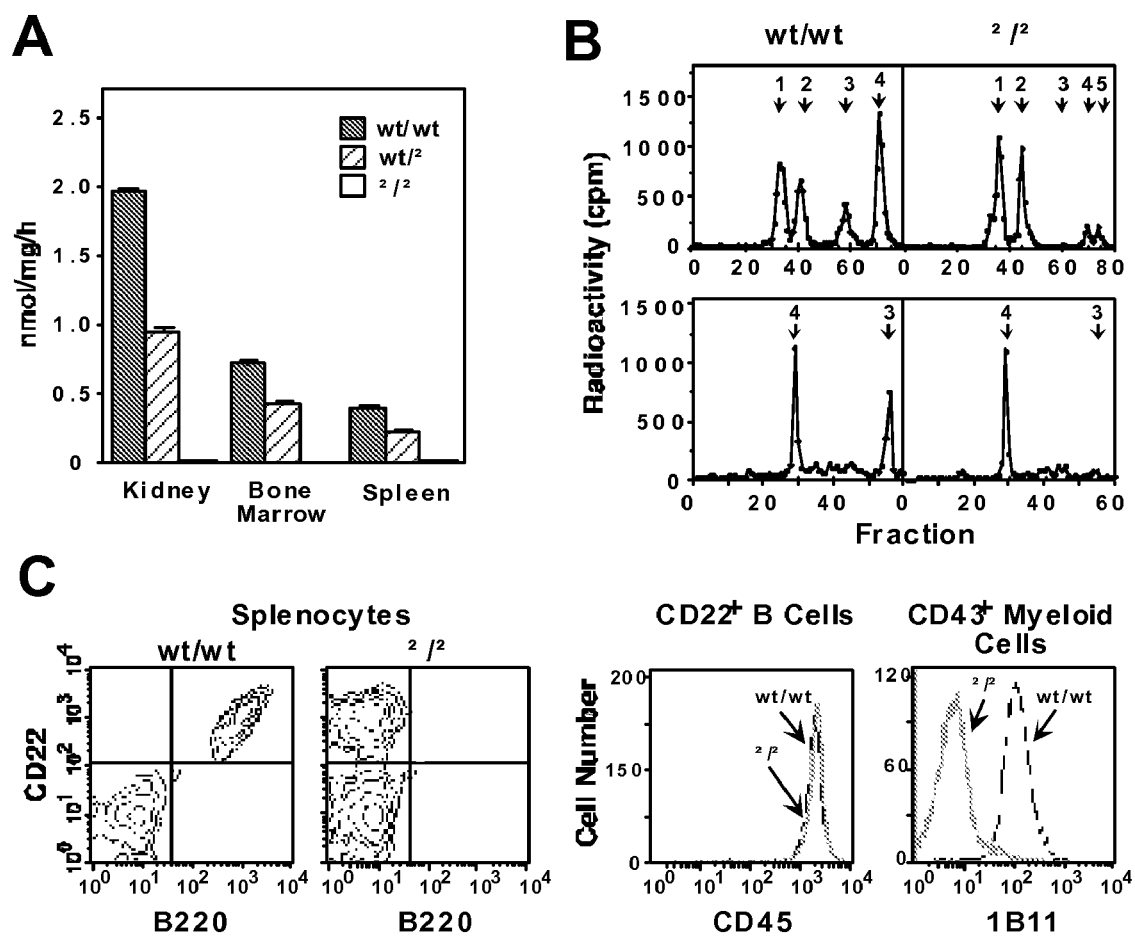
FIG. 10A-FIG. 10C demonstrate C2GlcNAcT activity and oligosaccharide production.

C2 GlcNAcT enzyme activity was specifically detected by using a substrate analogue of the core 1 oligosaccharide (Yousefi et al. (991) *J. Biol. Chem.* 266: 1772-1782). In mice homozygous for the C2 GlcNAcT$^{\Delta}$ allele, tissues normally expressing high C2 GlcNAcT levels were devoid of significant activity, including the spleen, bone marrow and kidney (FIG. 10A). To determine whether loss of C2 GlcNAcT activity resulted in a deficiency of core 2 O-glycans, oligosaccharide structures were analyzed in metabolically-labeled splenocytes. O-linked oligosaccharides isolated from splenocytes homozygous for the C2 GlcNAcT$^{\Delta}$ allele lacked Galβ1-3 (Galβ1-4GlcNAcβ1-6)GalNAc, indicating a deficiency of core 2 O-glycans (FIG. 10B upper panel, peak 3). Desialylation and additional chromatographic analysis further indicated a loss of core 2 O-glycans (FIG. 10B lower panel, peak 3). The majority of core 1 oligosaccharides in C2 GlcNAcT deficient splenocytes were sialylated, consistent with structures expected in the absence of C2 GlcNAcT activity.

Monoclonal antibodies previously implicated as oligosaccharide-dependent were also applied to characterize C2 GlcNAcT deficient cells. B lymphocytes specifically express CD22 and the B cell epitope B220 the latter of which is a glycoform of CD45 (Johnson et al. (1989) *J. Exp. Med.* 169: 1179-84). Splenocytes lacking C2 GlcNAcT activity were devoid of the B220 epitope, while CD22 and CD45 protein levels at the cell surface were unaltered (FIG. 10C, left panels). The CD43 glycoprotein is highly expressed on leukocytes as two distinct glycoforms differentially recognized by monoclonal antibodies S7 and 1B11. The high molecular weight CD43 glycoform expressed on myeloid cells is modified with core 2 O-linked oligosaccharides and is recognized by the 1B11 antibody (Jones et al. (1994) *J. Immunol.* 153: 3426-3439). In mice homozygous for the C2 GlcNAcT$^A$ allele, myeloid cells remained positive for S7 binding, while 1B11 antibody binding was distinctly absent (FIG. 10C, right panels). These data reveal that homozygosity at the C2 GlcNAcT$^A$ allele results in a deficiency of C2 GlcNAcT activity and core 2 O-glycans.

C. C2 GlcNAcT Deficiency Results in a Moderate Neutrophilia

Figure 11:
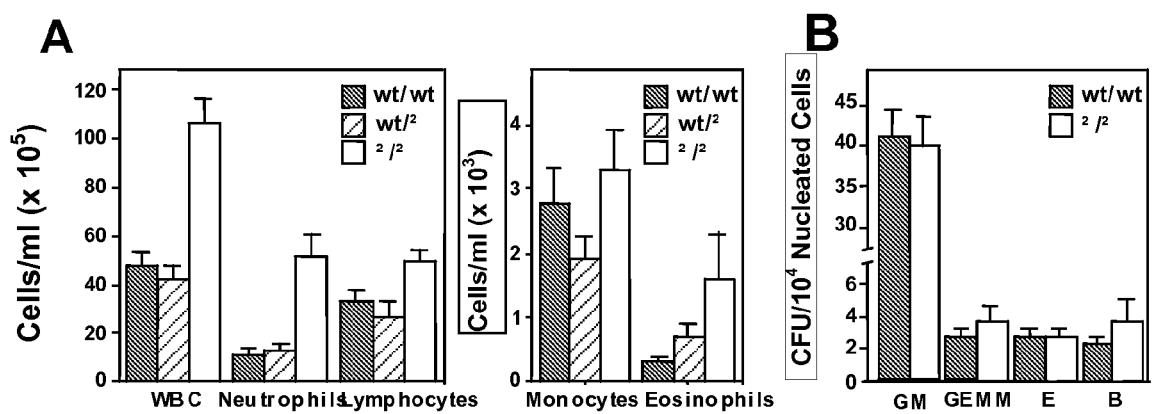
FIG. 11A and FIG. 11B show the peripheral hematology in C2 GlcNAcT deficient mice. Blood was collected from the tail vein of 6-8 week old mice. Automated total white blood cell counts and automated and manual differential counts were carried out using a CELL-DYN 3500 and Wright-Giemsa stained smears. Counts from 20 mice of each genotype are expressed as cells per ml of whole blood± SEM.
FIG. 11C shows colony forming units in the bone marrow, which were analyzed by in vitro differentiation of nucleated bone marrow cells in methylcellulose in the presence of growth factors. The number of colony-forming units (GM—granulocyte/macrophage; GEMM—granulocyte/erythroblast/macrophage/monocyte; E—erythroblast; B-B cell) was counted at day 10. Data are means± SEM from 6 mice of each genotype.

Upon histologic examination, no alterations were detected in cellular or organ morphologies within C2 GlcNAcT deficient mice. The kidney, lungs, the intestinal tract, and associated epithelium were unremarkable and mucin levels in the intestinal goblet cells were indistinguishable from controls. Analyses of serum biochemistry indicated normal renal function. Hematologic examination disclosed a blood leukocytosis. Total white blood cell counts were elevated 2.4 fold in C2 GlcNAcT null mice. This increase was almost entirely accounted for by a 4.3 fold increase in neutrophils (FIG. 11A). Bone marrow progenitor cell numbers were normal in C2 GlcNAcT null mice, implying that the leukocytosis is not a consequence of increased neutrophil production (FIG. 11B). In other studies, circulating platelet levels and morphology were also unchanged and no difference in bleeding time was apparent. These observations are reminiscent of certain results obtained from mice deficient in selectins or selectin ligands.

D. C2 GlcNAcT Participates in Selectin Ligand Formation and Leukocyte Rolling

Figure 12:
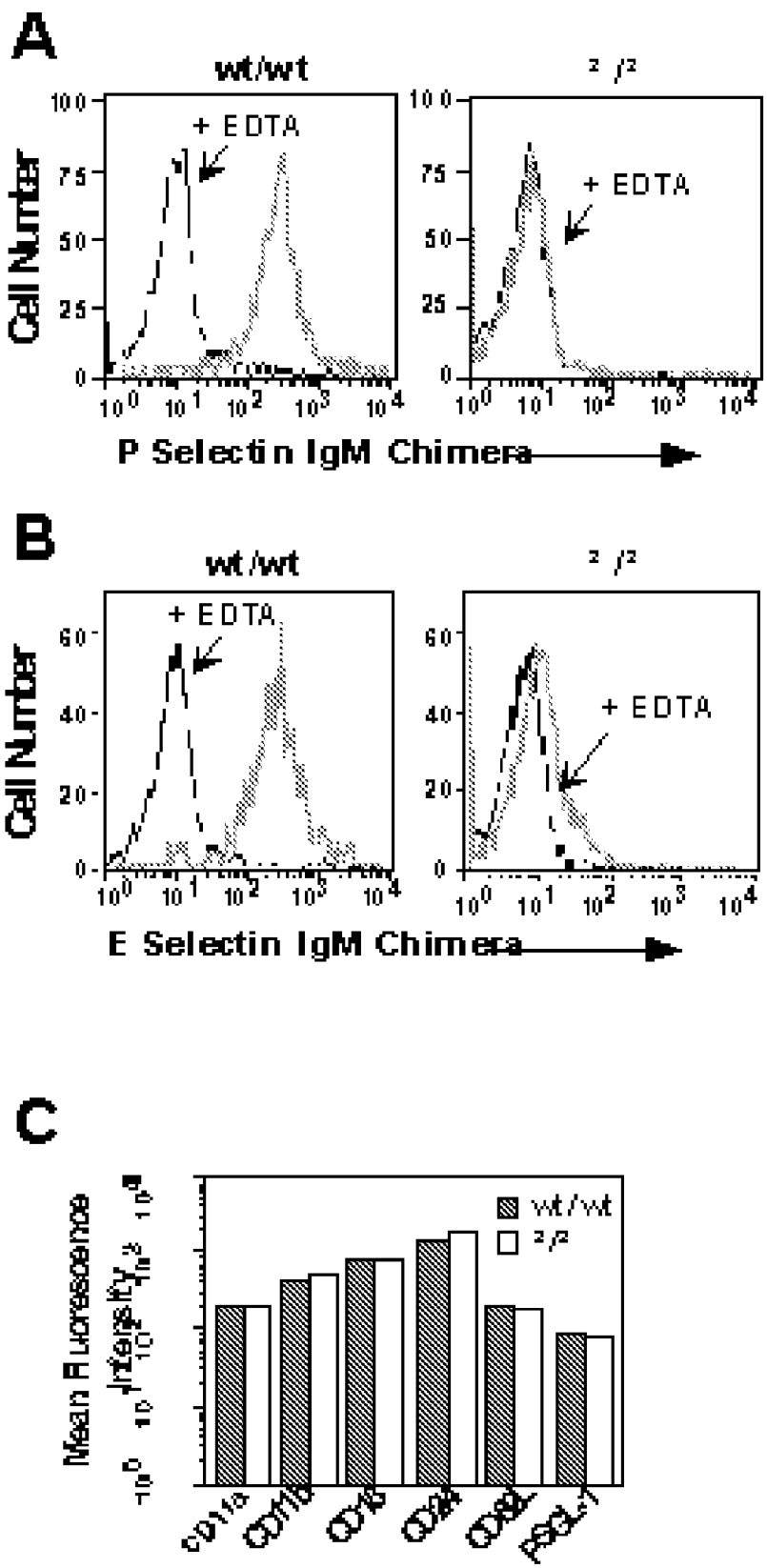
FIG. 12A-C show leukocyte selectin ligand expression.

To detect a role for C2 GlcNAcT in selectin ligand biosynthesis, selectin-Ig chimeras were used to examine levels of E-, L- and P-selectin ligands on cell surfaces. The E- and P-selectin chimeras specifically bind to carbohydrate ligands on myeloid cells in the blood including granulocytes and monocytes (Maly et al. (1996) *Cell* 86: 643-653). Using flow cytometry, peripheral blood leukocytes from C2 GlcNAcT null mice were found to be deficient in both E- and P-selectin ligands. The P-selectin chimera did not significantly bind whereas a low level of E-selectin-Ig binding remained (FIG. 12A). These results were not due to reduced expression of proteins that carry selectin ligands. Cell surface levels of PSGL-1, L-selectin and CD24 on C2 GlcNAcT deficient leukocytes were unaffected, as were levels of various adhesion molecules involved in the firm attachment of leukocytes to the endothelium (CD11a, CD11b and CD18; FIG. 12B).

A parallel plate flow chamber system was used to measure the contribution of core 2 oligosaccharides to functional selectin binding. Immobilized E-, L- or P-selectin-Ig chimeras served as the adhesion substrate for neutrophil rolling in this system. The binding of FucT-VII null leukocytes was monitored in direct comparisons as they do not appreciably bind selectins at most shear forces (Maly et al. supra.). Leukocytes deficient in core 2 oligosaccharides exhibited reduced but significant rolling activity on E- and P-selectins at all shear forces used, while FucT-VII null leukocytes did not interact appreciably with the immobilized selectin-Ig chimeras (FIG. 12C). At the highest shear forces, 50% of C2 GlcNAcT null leukocytes remained bound to the P-selectin substrate and approximately 20% bound to the E-selectin substrate. In contrast, leukocyte rolling on L-selectin appeared especially dependent upon core 2 oligosaccharide biosynthesis as C2 GlcNAcT deficient leukocytes were unable to bind except at shear forces below 10 dynes/cm$^2$.

E. Core 2 Oligosaccharides Recruit Neutrophils to Sites of Inflammation

Since core 2 oligosaccharides contribute to selectin ligand biosynthesis, it seemed likely that C2 GlcNAcT null mice would exhibit abnormalities in lymphocyte trafficking and neutrophil recruitment to sites of inflammation. During the first four hours following an inflammatory stimulus, neutrophil recruitment to sites of inflammation is largely dependent upon selectin function (Mayadas et al. (1993) *Cell* 74: 541-554). Peritonitis induced by thioglycollate injection can be used to assess selectin function in a model of acute inflammation involving quantitation of neutrophil recruitment in vivo. In the absence of core 2 oligosaccharides, a severe deficit in neutrophil recruitment to inflamed peritoneum was apparent with only 20% of control neutrophil numbers recoverable at 4 hours (Table 2). This extent of reduction in neutrophil numbers is similar in FucT-VII deficient mice which are more deficient in selectin ligand formation (Maly et al., supra.). These data indicate that core 2 oligosaccharides provide an essential function in selectin-mediated neutrophil recruitment during acute inflammation.

TABLE 2

| Neutrophil Recruitment to Peritoneal Exudates during Inflammation | | |
|---|---|---|
| Hours Post-Stimulus | C2 GlcNAcT$^{wt/wt}$ | C2 GlcNAcT$^{\Delta/\Delta}$ |
| 0 | 4 ± 1 (n = 3) | 4 ± 1 (n = 3) |
| 2 | 48 ± 6 (n = 10) | 5 ± 1 (n = 7)* |
| 4 | 499 ± 86 (n = 10) | 96 ± 19 (n = 12)* |

Data are the means ± SEM of neutrophil numbers (×10$^4$) recovered from the peritoneal lavage of thioglycollate-treated mice.
The number of mice in each group is indicated in parentheses.
An unpaired t test indicated significance of * p < 0.001.

Figure 13:
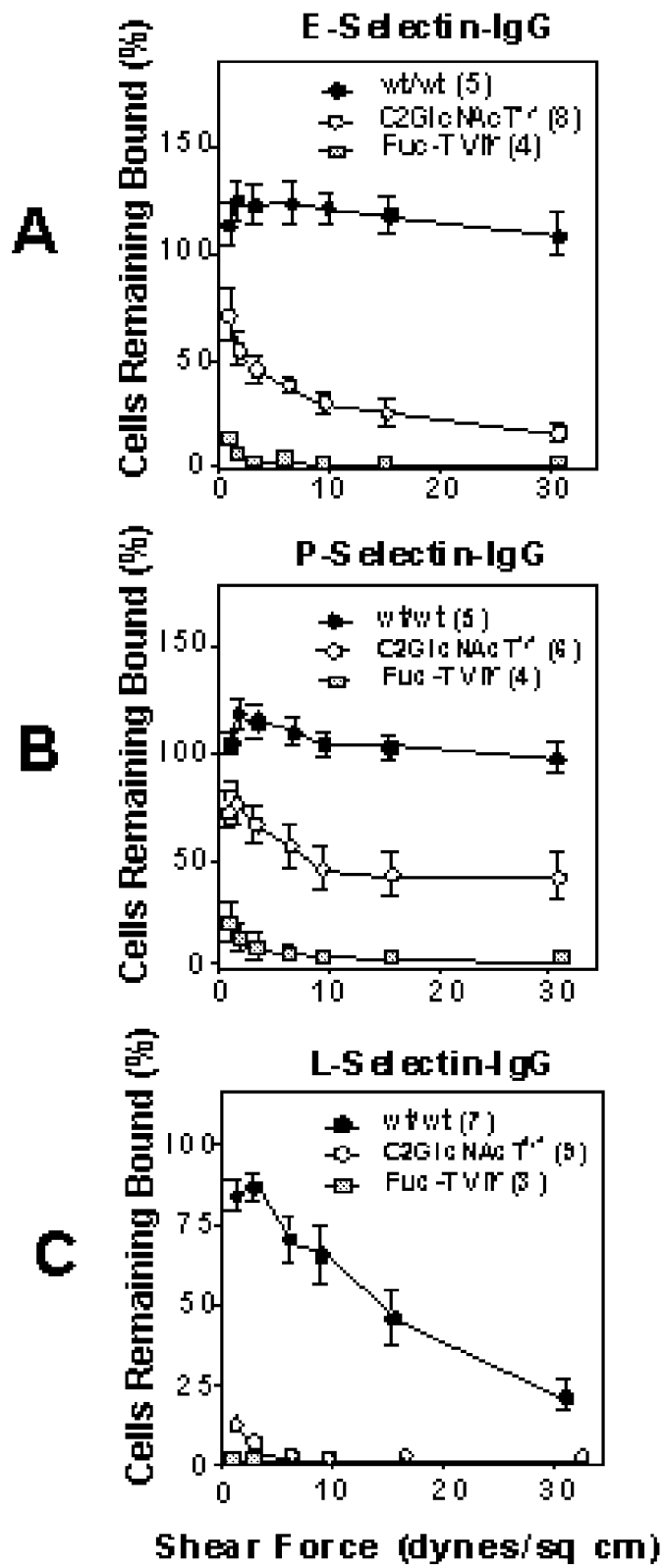
FIG. 13A-FIG. 13C show results of an analysis of lymph node morphology, L-selectin binding and lymphocyte homing.
Figure 14:
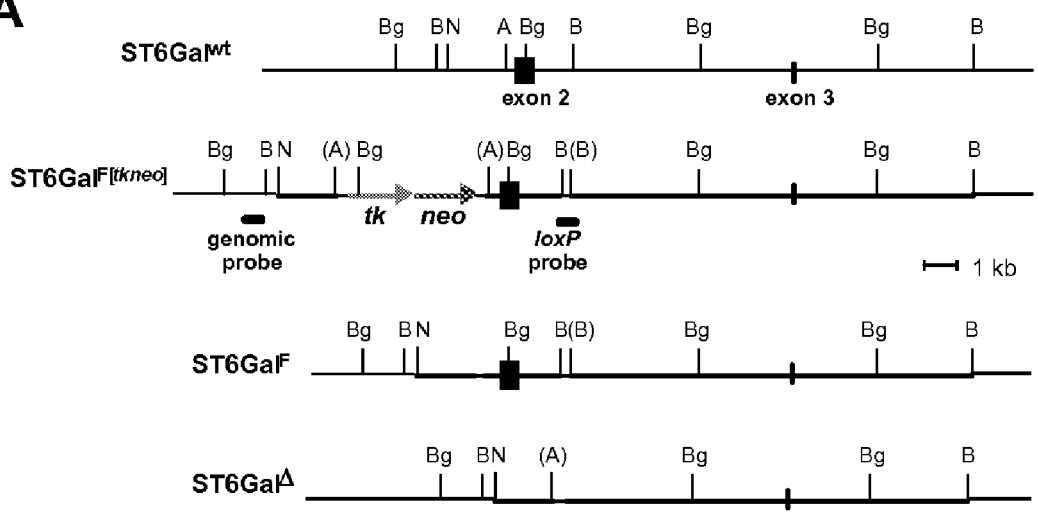
FIG. 14A is a schematic diagram of the ST6Gal genomic structure and the construction of ST6Gal mutants. A partial ST6Gal genomic structure (ST6Gal$^{wt}$) was cloned and used with pflox in constructing a targeting vector (bold line) shown recombined at the ST6Gal locus (ST6Gal$^{F[tkneo]}$) locus in ES cell clone 4.8). Following Cre recombinase expression and ganciclovir selection, ES cell subclones B3 and B9, bearing the ST6Gal$^F$ and the ST6Gal$^\Delta$ allele, respectively, were isolated and used in generating chimeric mice.
FIG. 14B shows genomic Southern blots of ST6Gal alleleic structure in wild-type (wt) ES cells, targeted ES cell clone 4.8 (ST6Gal$^{F[tkneo]}$), 4.8 ES cell subclone B3 (ST6Gal$^F$), and 4.8 ES cell subclone B9 (ST6Gal$^\Delta$) using either a genomic probe outside the targeting vector (left) or a loxP probe (center). At right is shown a genomic Southern blot analysis of offspring derived from matings of mice heterozygous for the ST6Gal$^\Delta$ allele. Genotypes include the presence of mice homozygous for the exon 2 deletion (ST6Gal$^\Delta$).
FIG. 14C presents fluorescent activated cell sorting (FACS) analyses using SNA and CD22-Ig lectins which shows that splenic CD3$^+$ and B220$^+$ lymphocytes specifically express high levels of Sia6LacNAc in comparison with GR-1+ myeloid and Ter-119+ erythroid cells. Lymphocytes from mice homozygous for the B9-derived ST6Gal$^\Delta$ allele were deficient in Sia6LacNAc (n=7). α2,3-linked sialic acids were detected using the MAL II lectin and were found to be expressed at low levels normally and unaltered among cells from mice homozygous for the ST6Gal$^\Delta$ allele (n=7). Mice homozygous for the B3-derived ST6Gal$^F$ allele displayed wild-type profiles in these lectin-based analyses. Similar results were obtained with mesenteric lymph node-derived lymphocytes. Fluorescence signal intensity using an anti-human IgG-FITC conjugate is shown (2° and dotted line, lower left).
Figure 14:
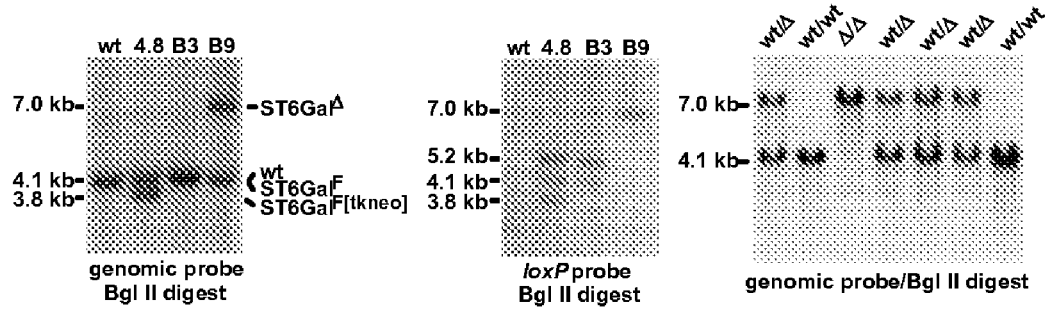
Figure 14:
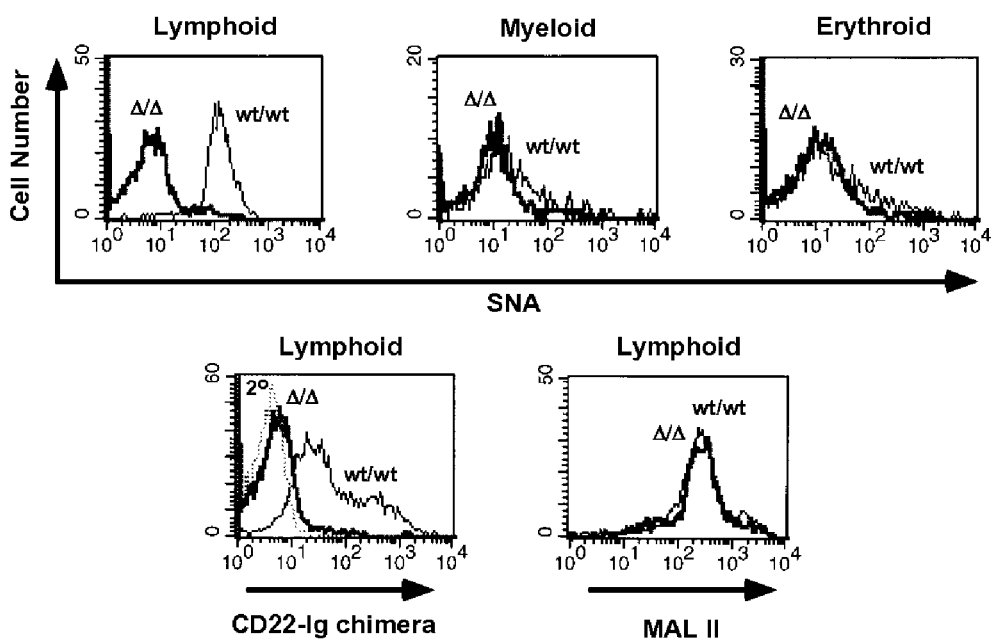
Figure 15:
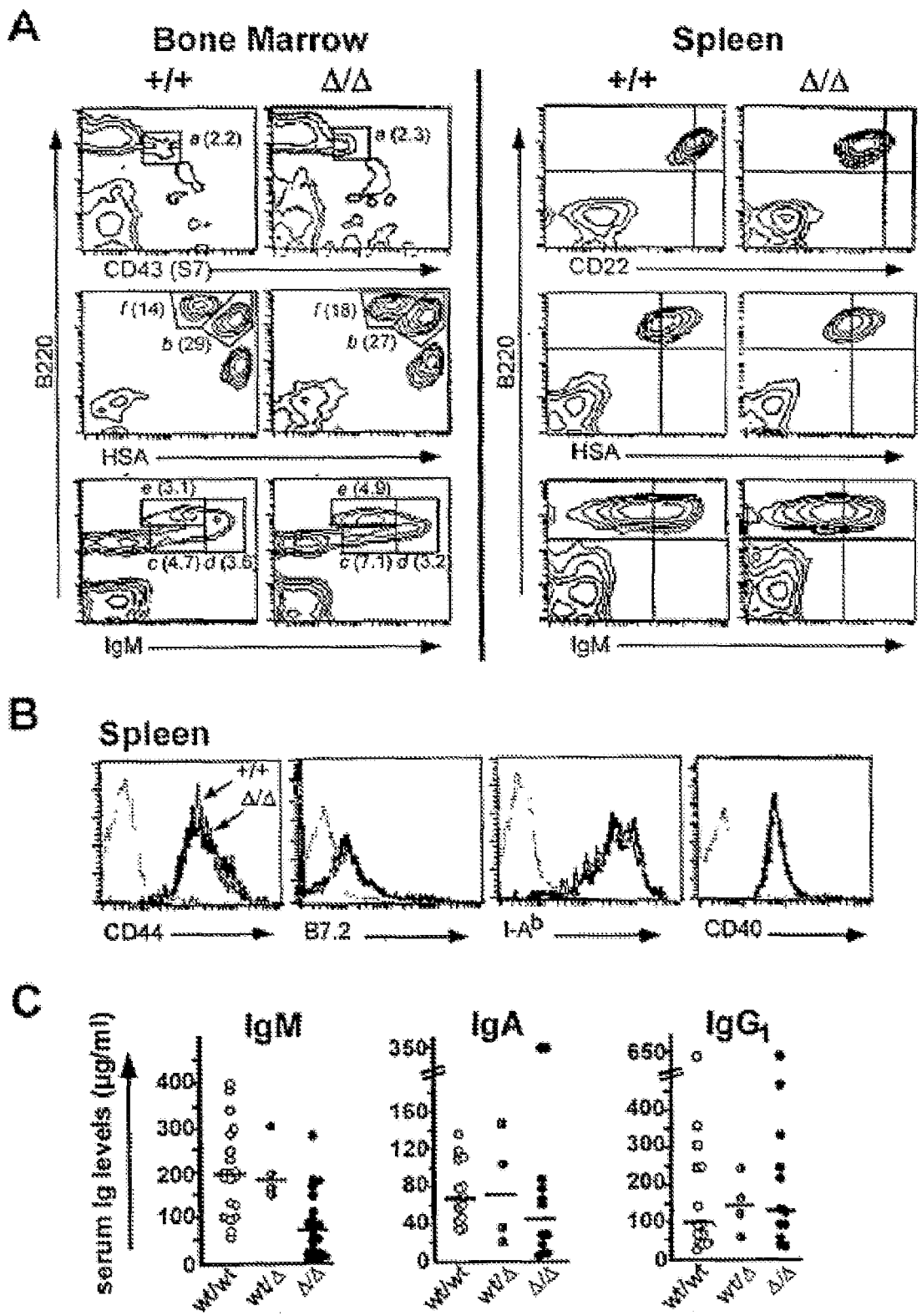
FIG. 15A-15C show B lymphocyte characterization and serum immunoglobulin analyses.
Figure 16:
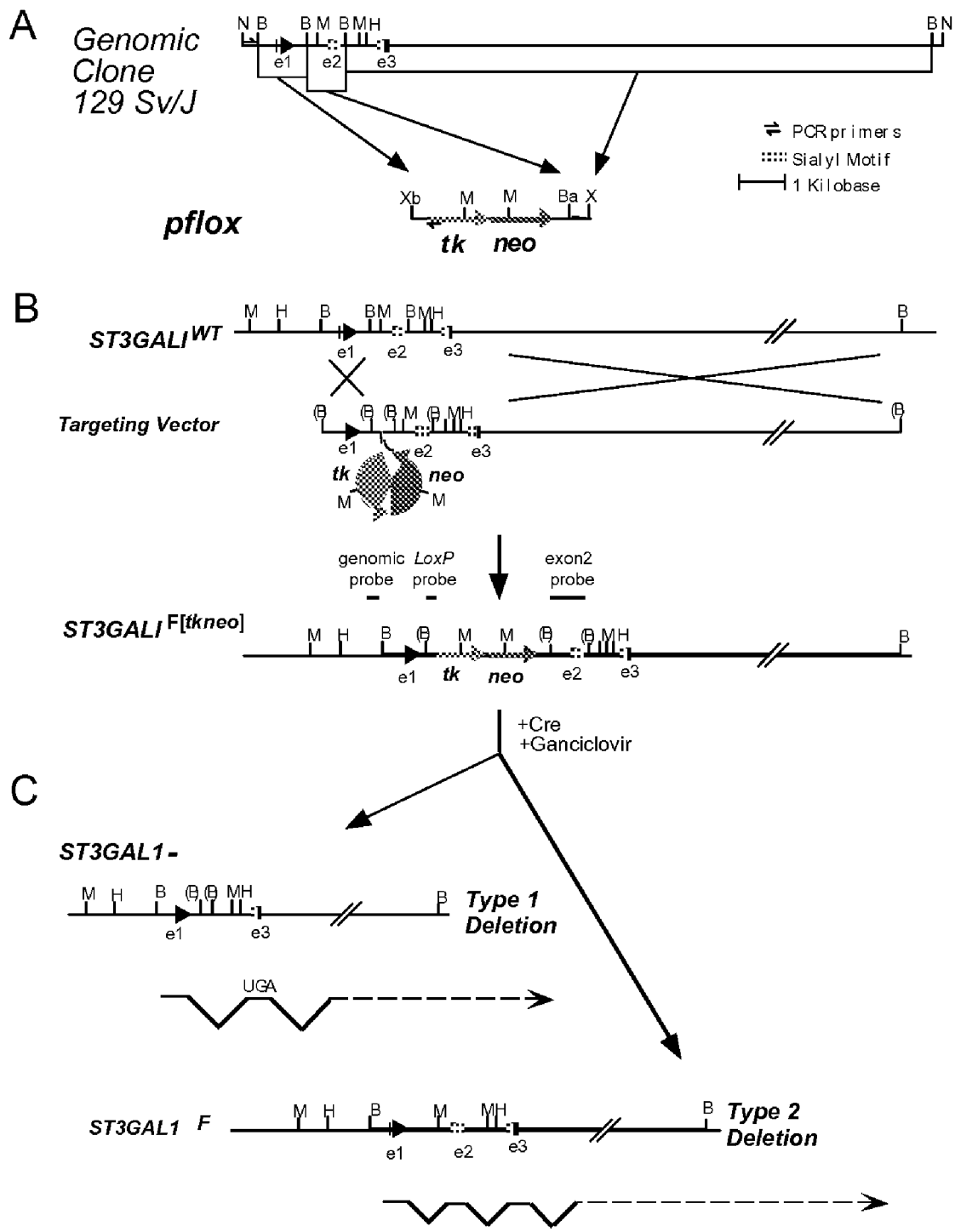
FIG. 16A-16C presents a schematic diagram of the ST3Gal I gene structure and the construction of ST3Gal I mutants.

F. L-Selectin Ligands Produced by C2 GlcNAcT are Dispensable for Lymphocyte Homing L-selectin and FucT-VII are crucial for lymphocyte homing to the lymph nodes (Arbones et al. (1994) *Immunity* 1: 247-260; Maly et al., supra.). Since L-selectin counter-receptors on HEVs may be sialylated mucins, it seemed likely that C2 GlcNAcT was involved in their production. However, secondary lymphoid organs from C2 GlcNAcT deficient mice exhibited normal tissue size and follicular anatomy without alterations in either lymphocyte abundance or subset proportions (FIG. 13A). Nevertheless, L-selectin binding to lymph node HEVs was reduced in the absence of C2 GlcNAcT (FIG. 13B). This deficit in L-selectin ligand formation was not apparent using higher concentrations of the L-selectin-Ig chimera (data not shown) and was without significant consequence as lymphocyte homing to C2 GlcNAcT deficient lymph nodes and spleen was statistically unaltered (FIG. 13C and data not shown). These results indicate that C2 GlcNAcT activity in HEV L-selectin biosynthesis is dispensable for lymphocyte homing to secondary lymphoid organs.

Discussion

The C2 GlcNAcT glycosyltransferase is essential for the biosynthesis of core 2 O-glycans in leukocytes. Loss of C2 GlcNAcT provides a unique model of selectin ligand deficiency that results in a deficit in the inflammatory response while lymphocyte homing remains intact. Defining the structural basis of physiologic selectin ligands is of continued relevance as this study reveals that selectin ligand biosynthesis and function are differentially regulated among various anatomic compartments. Some glycosyltransferases and glycosidases have been found to function with a significant degree of cell-type specificity (Maly et al. (1996) *Cell* 86: 643-653; Chui et al. (1997) *Cell* 90: 157-167; Hennet et al. (1998) *Proc. Nat'l. Acad. Sci. USA* 95: 4504-4509), and C2 GlcNAcT appears to be dedicated to a role involving selectin-mediated responses of myeloid cells.

A. Core 2 Oligosaccharides in the Biosynthesis of Selectin Ligands

C2 GlcNAcT operates differentially in E-, L- and P-selectin ligand formation. The deficiency of E- and P-selectin-Ig binding to core 2 O-glycan deficient leukocytes observed by flow cytometry was tempered by data from neutrophil rolling assays which revealed significant residual binding on both E-and P-selectin substrates. Additionally, a small amount of L-selectin binding remained in comparison to FucT-VII null leukocytes, but only at the lowest shear forces applied. All three selectins can bind to PSGL-1 and it is possible that PSGL-1 acts as the major selectin counter-receptor in the rolling assay. Residual E- and P-selectin binding by C2 GlcNAcT deficient leukocytes indicates a possible role for N-glycans in physiologic selectin ligand formation. The CD24 glycoprotein is extensively N-glycosylated on myeloid cell surfaces where it has been reported to mediate binding of monocytes and neutrophils to P-selectin (Aigner et al. (1995) Int. Immunol. 7: 1557-1565). In addition, the E-selectin counter-receptor, ESL-1 contains only N-linked oligosaccharides and has been found on leukocyte microvilli where it may regulate initial cell adhesion events (Steegmaier et al. (1997) J. Cell. Sci. 110: 687-94). Leukocyte L-selectin ligand production appears to be greatly dependent upon core 2 oligosaccharide formation, which may be particularly relevant in secondary interactions involving neutrophil-neutrophil binding at sites of inflammation and extravasation (Walcheck et al. (1996) J. Clin. Invest. 98: 1081-7). Our studies indicate that although C2 GlcNAcT provides a significant proportion of E-, L- and P-selectin ligands on leukocytes, it is not as essential as is FucT-VII. Therefore other oligosaccharide substrates of FucT-VII that are not produced by C2 GlcNAcT are also involved in selectin ligand biosynthesis.

B. The Physiologic and Cell-Type-Specificity of C2 GlcNAcT among Leukocytes

With E- and P-selectin binding evident in shear flow studies of C2 GlcNAcT null neutrophils, the decrease observed in neutrophil recruitment during peritoneal inflammation was surprisingly severe. The extent of the reduction is similar to that observed in the absence of FucT-VII with an 80% reduction in neutrophil recruitment. Not all neutrophil recruitment to inflamed peritoneum requires selectins or FucT-VII. Approximately 20% of neutrophils recruited during the first four hours of acute inflammation may be accounted for by the function of the intercellular adhesion molecule-1 (ICAM-1; Kunkel et al. (1996) J. Exp. Med. 183: 57-65). These findings imply that selectin and FucT-VII involvement in acute inflammation are dependent upon C2 GlcNAcT and core 2 oligosaccharides.

Altered leukocyte homeostasis in C2 GlcNAcT deficient mice is intermediate in severity in comparison to studies of P-selectin and FucT-VII deficiencies. The major hemodynamic effect in the absence of C2 GlcNAcT was an increase in neutrophil levels. An absence of P-selectin results in a small increase in peripheral neutrophils, but no change in total leukocytes (Mayadas et al. (1993) Cell 74: 541-554), whereas mice deficient in either E- or L-selectin exhibit normal peripheral hematologic profiles (Arbones et al. (1994) Immunity 1: 247-260; Labow et al. (1995) Immunity 1: 709-720). When both P- and E-selectins are missing (Frenette et al., 1996) or in the absence of FucT-VII (Maly et al. (1996) Cell 86: 643-653), marked increases in leukocytes are observed, above that measured in C2 GlcNAcT deficient mice. Bone marrow progenitor frequencies were unaltered in C2 GlcNAcT deficient mice, suggesting an increase in neutrophil half-life may account for the neutrophilia as was reported with P-selectin deficiency (Johnson et al. (1995) Blood 86: 1106-14). In contrast to results reported in the absence of P-selectin, C2 GlcNAcT deficient mice exhibited a normal bleeding time (Subramaniam et al. (1996) Blood 87: 1238-1242; data not shown).

The selective nature of C2 GlcNAcT function was further evident from studies of lymph node morphology and lymphocyte homing. The partial deficit observed in L-selectin binding to lymph node HEVs appeared inconsequential as lymphocyte abundance and homing was not affected. Perhaps physiologic L-selectin ligands are normally expressed in over-abundance and the quantity remaining in C2 GlcNAcT deficient mice is sufficient to facilitate normal lymphocyte homing. It is also possible that the HEV glycoproteins modified by C2 GlcNAcT to carry L-selectin ligands do not participate in lymphocyte homing. As L-selectin ligands may exist on separate oligosaccharide classes (N-glycans, O-glycans, glycolipids, etc.), the underlying structures in these classes may influence their presentation and the efficacy of function in binding L-selectin in vivo. L-selectin counter-receptors implicated in lymphocyte homing include sialylated mucins such as CD34. Their identity is uncertain and CD34 deficient mice exhibit normal lymphocyte homing (Cheng et al. (1996) Blood 87: 479-90; Suzuki et al. (1996) Blood 87: 3550-62). A possibility that other oligosaccharide classes are involved is consistent with the observation that O-sialoglycoprotease-resistant L-selectin ligands exist on lymph node HEVs (Clark et al. (1998) J. Cell. Biol. 140: 721-31). While the structural features of physiologic L-selectin ligands remain to be fully established, the oligosaccharides involved in lymphocyte homing are dependent upon the function of FucT-VII but do not require C2 GlcNAcT, and thus may not be composed of core 2 oligosaccharides.

C. C2 GlcNAcT in Oligosaccharide Diversification and Function

The C2 GlcNAcT glycosyltransferase is essential for generating core 2 O-glycans in the kidney, bone marrow and peripheral leukocytes. Since C2 GlcNAcT can also act on glycolipid substrates (Piller et al. (1984) J. Biol. Chem. 259: 13385-90), it is possible that the phenotypes manifested may be due in part to a deficiency of specific glycolipids that are substrates of C2 GlcNAcT in the Golgi. We also cannot rule out the possibility that a distinct gene product encoding a C2 GlcNAcT isozyme is expressed in specific compartments such as lymph node HEVs and which may account for functional L-selectin ligand formation. Several studies have suggested the presence of such an isozyme in mucin producing tissues that is capable of synthesizing both core 2 and core 4 O-glycans (Kuhns et al. (1993) Glycoconj. J. 10: 381-94; Ropp et al. (1991) J. Biol. Chem. 266: 23863-71). Although core 4 O-glycans may partially compensate for C2 GlcNAcT deficiency, C4 GlcNAcT activity is not normally found in myeloid cell types (Bierhuizen and Fukuda (1992) Proc. Nat'l. Acad. Sci. USA 89: 9326-9330; Schachter and Brockhausen (1989) Symp. Soc. Exp. Biol. 43: 1-26), and core 4 activity was not induced in tissues from C2 GlcNAcT deficient mice (data not shown).

The function of C2 GlcNAcT in neutrophil recruitment during inflammation is consistent with a role in the biosynthesis of selectin ligands. E-, L- and P-selectin ligand production is only partially C2 GlcNAcT-dependent, yet this partial dependence encompasses a potent and restricted physiologic activity. Inhibition of C2 GlcNAcT activity might provide a selective means to dampen acute inflammatory responses and reperfusion injury (Lowe and Ward (1997) J. Clin. Invest. 99: 822-826). Our results imply that core 2 O-glycans provide an unexpectedly restricted biological function that may reflect the presence of additional glycosyltransferases with overlapping activities. The unique modulatory roles exerted by glycosyltransferases may arise through differential expression patterns that can affect levels of oligosaccharides and their structural presentation by core and glycoprotein components.

Either possibility may explain how the C2 GlcNAcT glycosyltransferase selectively regulates myeloid homeostasis and inflammation.

Example 3

Diagnosis of CDA Type II/HEMPAS

This Example describes the diagnosis of CDA Type II/HEMPAS by detecting loss of E-PHA binding to red blood cells.

A transgenic mouse deficient in α-mannosidase-II was obtained. These mice exhibit a dyserythropoietic anemia similar to that observed in CDA Type II/HEMPAS. Only erythroid cells were affected with the deficiency in glycosylation, as all other cell types use an alternative pathway that does not involve α-mannosidase-II.

α-mannosidase-II deficiency was diagnosed by observing a severe reduction in E-PHA binding to whole blood, but not usually in plasma or serum. Increased tomato lectin reactivity (binds to polylactosamines) was also diagnostic, and was not found in CDGS Type II.

Example 4

Diagnosis of Immunodeficiency Associated with B Lymphocyte Deficiency

This Example demonstrates that SNA and CD22-Ig lectins which specifically bind the Siaα2-6Galβ1-4GlcNAc (Sia6LacNAc) trisaccharide can be used to diagnose immune system dysfunction in mice. Mice deficient in Sia6LacNAc were created by deletion of the sialyltransferase gene responsible for the synthesis of Sia6LacNAc, ST6Gal I. SNA and CD22-Ig lectins were used to detect the presence or absence of the Sia6LacNAc trisaccharide on the surface of various cell types. Cells that lack the ST6Gal I gene were found to not express the Sia6LacNAc trisaccharide on the surface of lymphocytes, while the trisaccharide was detected on the surfaces of lymphocytes from cells that were not defective for ST6Gal I. The ST6Gal I deficient mice displayed a marked immunodeficiency characterized by a deficit in B cell activation.

A. Materials and Methods

1. ST6Gal Gene Targeting

Mice harboring a mutated ST6Gal-I gene were generated from embryonic stem cells following a targeted deletion of ST6Gal-I exon 2 containing the N-terminal 200 amino acids of the encoded sialyltransferase. The ST6Gal I targeting vector was assembled from a 129/Sv genomic clone by inserting the 1.9 kb Acc I-Bam HI fragment containing exon 2 of ST6Gal I encoding the first 200 amino acids into the Bam HI site of the pflox vector ( ). Adjacent 129/Sv ST6Gal I genomic sequences were added by subcloning the 1.8-kb Nhe I-Acc I fragment into the Sal I site and the Bam HI-Bam HI 12 kb fragment into the Hind III site of pflox, respectively. Ten μg of Not I-linearized targeting vector were electroporated into ES cells and G418 resistant transfectants (120 μg/ml), positive by PCR for homologous recombination and which retained all three loxP sites were transfected with Cre expression vector. Following four days of gancyclovir (2 μM) selection, subclones were isolated and those bearing either the ST6Gal$^F$ allele (B3) or the ST6Gal I$^\Delta$ allele (B9) were confirmed by Southern blotting with loxP and Hind III-Hind III genomic probes. B3 and B9 ES cells were used to generate chimeric mice in C57BL/6 host embryos. Offspring were genotyped by Southern blotting with Bgl II-digested tail DNA hybridized to the Hind III-Hind III 500 bp genomic probe. Heterozygous offspring were mated to C57BL/6 mates and the mutations were propagated in this strain for at least two generations before crosses to produce homozygotes for experimentation. The ST6Gal I mutation was maintained in the C57BL/6 inbred line for 3-5 generations prior to analyses. The phenotypes described were found linked to mice bearing the homozygous ST6Gal$^\Delta$ mutant phenotype in subsequent studies involving more than four generations. Mice homozygous for the ST6Gal$^F$ genotype did not display any phenotypic consequences and as expected contained normal levels of Sia6LacNAc.

Deletion of ST6Gal-I exon 2 results in loss of cytoplasmic, transmembrane and considerable catalytic domain sequences, such that any translated truncated enzyme would also be incapable of entry into the lumen of the endoplasmic reticulum and Golgi. Mice homozygous for the ST6Gal-I$^\Delta$ deletion were born at Mendelian frequency and appeared grossly normal throughout post-natal development.

2. Detection of Presence or Absence of Sia6LacNAc by Fluorescence-Activated Cell Sorter Analysis using SNA and CD22-Ig Lectins ST6Gal-I function was assessed in assays using SNA and CD22-Ig lectins which specifically bind the Siaα2-6Galβ1-4GlcNAc (Sia6LacNAc) trisaccharide found on various asparagine (N)-linked oligosaccharides. Single cell suspensions from the spleen, thymus, lymph node and bone marrow were subjected to ammonium chloride lysis of red cells. Cells were counted with a hemocytometer and 500,000 cells were labeled in a final volume of 100 μl with either SNA-FITC (5 μg/ml; Vector Laboratories), or MAL II-FITC (5 μg/ml; Vector Laboratories) and/or 1 μl of monoclonal antibody or CD22-Ig chimera for 10 minutes. All incubations and washes were performed on ice in FACS buffer (2% FCS in PBS). Cells were analyzed using a "FACScan" Flow Cytometer and Cellquest Software (Becton Dickinson). Serum isotype-specific antibody titres were determined by ELISA using plates coated with anti-mouse isotype specific antibodies. A standard curve was generated using purified mouse IgM, IgA (Sigma), and IgG$_1$ (PharMingen) to convert OD values to μg/ml. Antibodies and lectins used in the course of these and other studies herein included (all from PharMingen unless otherwise noted): anti-CD3 (2C11), anti-CD4 (RM4-5), anti-CD8 (53-6.7), anti-CD11b-FITC or –PE (Mac-1, M1/70), anti-CD21.35 (7G6), anti-CD22-PE (Cy34.1), anti-CD23 (B3B4), anti-CD43 (S7), anti-CD44 (IM7), anti-B7.2 (G1.1), anti-B220-PE (RA3-6B2), anti-mouse IgM-biotin (II/41), anti-mouse IgD-FITC (11-26c.2a), anti-CD24 (HSA)-FITC (M1/69), anti-CD40-FITC (HM40-3), anti-CD19-FITC (1D3), anti-mouse 1-A$^b$-FITC (AF6-120.1), anti-erythroid (Ter-119); anti class I MHC (KH95), anti-Ly-6G (Gr-1)-PE (RB6-8C5) (Pharmingen), SNA-FITC, ECA-FITC, and PNA-FITC (Vector Laboratories). In FACS analyses, biotinylated antibodies were detected using Streptavidin-Tri-Color (CalTag, South San Francisco Calif.). The CD22-hIg fusion chimera was as described in Stamenkovic et al., *Cell*, 66:1133 (1991).

3. ST6Gal Sialyltransferase Activity Measurements

Tissue samples were homogenized in 3 ml of 500 mM sucrose, 1 mM MgCl$_2$, 1% dextran, 5 mM 2-mercaptoethanol. After removal of cell debris at 10,000×g, membranes were isolated by centrifugation at 40,000 rpm in a Beckman SW50.1 rotor for 1 hr. Membranes were solubilized in 25 mM cacodylate buffer (pH 6.8)/2% Triton X-100 for 15 min on ice. The membrane and cytosolic fractions (12.5 μl) were analyzed for sialyltransferase activity in 25 μl assays with 25 mM cacodylate (pH 6.8), 0.4 mM CMP-sialic acid (Sigma), 10$^5$ cpm of CMP-[$^{14}$C]sialic acid (170 pmol) (Amersham), and 1 mM LacNAc-octyl. Reactions were incubated at 37° C. for 1 hr. Products were separated from unincorporated sialic acid by chromatography on Sep-Pak $C_{18}$ cartridges (Waters), dried by centrifugal evaporation, redissolved in 50 µl of 50 mM sodium citrate buffer (pH 6.0), and incubated for 1 hr at 37° C. after the addition of two units *Salmonella typhimurium* LT2 sialidase (New England Biolabs). The digestion products were applied to SepPak $C_{18}$ cartridges, washed with 15 ml of $H_2O$, and eluted with 5 ml of methanol. The amount of $[^{14}C]$ sialic acid in the methanol eluates was measured in a liquid scintillation counter (RackBeta, Pharmacia). Separately, a recombinant soluble form of the human ST6Gal enzyme produced in *Pichia pastoris* was used in sialic acid transfer to the LacNAc-octyl acceptor and followed by the sialidase treatment described above. No significant cleavage was observed by loss of radiolabeling, thereby confirming the specificity of the LT2 sialidase for the α2,3 linkage when used in the above conditions. ST6Gal activity measurements undertaken with cytosolic fractions did not reveal any significant activity in either wild-type (wt) or mutant extracts.

4. B Cell Proliferation Assays

B lymphocyte isolation was accomplished by subjecting splenocytes or lymph node cell suspensions to complement mediated lysis with anti-Thy1.2 (Becton Dickinson), anti-Ly-6G (GR-1), and rabbit complement (Accurate Chemicals), followed by a cushion centrifugation onto NycoPrep (Life Technologies, Gaithersburg Md.) to remove debris and dead cells. Viable cells were identified by FACS as >90% B lymphocytes using anti-B220. Equivalent numbers of B cells of each genotype ($1\times10^5$) were cultured in complete RPMI 1640 medium containing 2-mercaptoethanol (0.1 mM), 10% FCS, and L-glutamine with the indicated concentrations of goat F(ab')2 anti-mouse IgM antiserum (Jackson, West Grove Pa.), anti-CD40 with or without IL-4 (Genzyme), or lipopolysaccharide (LPS) (Sigma). Proliferation was measured by $[^3H]$-thymidine incorporation (2.5 µCi per well) during the last 16 hr of a 64 hr assay period.

5. Calcium Measurements

Single cell suspensions of splenocytes were isolated and subjected to ammonium chloride red cell lysis. Cells were then counted using a hemocytometer and $10^7$ cells were incubated with 10 µM Indo-1 AM ester (Molecular Probes) at 37° C. for 30 min in 1 ml of complete RPMI 1640 medium. Cells were washed in FACS buffer and stained with FITC-conjugated anti-B220 (PharMingen) for 10 min at room temperature, washed again and resuspended in 1 ml of complete RPMI 1640 medium containing 10 mM Hepes (pH 7.4). Two hundred microliters of this suspension was added to 750 µl of RPMI-Hepes medium and B220+ cells were analyzed by FACS using a Coulter Elite (Coulter) with MULTITIME™ software (Phoenix Flow Systems, San Diego). Baseline fluorescence ratios (525/405 nm) were collected for one min before the addition of antibodies. The final concentrations of goat $F(ab')_2$ anti-mouse IgM used were 10 µg/ml and 30 µg/ml.

6. Protein Phosphotyrosine Analyses

Splenic B cells were isolated by complement-mediated lysis (see above) and $5\times10^5$ isolated B cells were resuspended in 50 µl of RPMI 1640 medium with 0.5% FCS. Cells were warmed to 37° C. before stimulation with 10 µl of goat $F(ab')_2$ anti-mouse IgM (120 µg/ml). At the indicated times, 15 µl of lysis buffer was added to give a final concentration of 1% Triton X-100, 50 mM Tris-HCl (pH 8.0), 150 mM NaCl, 1 mM EDTA, 10 mM NaF, 1 mM $Na_3VO_4$, 1 mM $Na_2MoO_4$, 2 µg/ml leupeptin, 2 µg/ml pepstatin, 2 µg/ml aprotinin, 5 µg/ml soybean trypsin inhibitor, and 40 µg/ml phenylmethylsulfonyl fluoride. Whole cell extracts representing $1\times10^5$ splenic B cells were run on a SDS/10% PAGE gel and transferred to nitrocellulose. Proteins phosphorylated on tyrosine were detected with monoclonal anti-phosphotyrosine antibody 4G10 (Upstate Biotechnology, Lake Placid N.Y.) by immunoblotting.

7. Immunizations and Serum Antibody Assays

Mice were prebled to obtain preimmune sera and subsequently immunized by i.p. injection of either 10 µg or 100 µg of dinitrophenyl (DNP)-keyhole limpet hemocyanin (KLH) (Calbiochem) in Freund's complete adjuvant, or 0.1 µg or 10 µg of dNP-Ficoll (Biosearch) in PBS. Serum was collected at the indicated times and anti-DNP titers were determined by ELISA using plates coated with 20 µg of DNP-BSA and blocked with 10% FCS in PBS. Mice receiving the DNP-KLH antigen were boosted at the indicated times with the same amount of antigen in Freund's incomplete adjuvant. Sera were diluted to various concentrations and analyzed using anti-mouse isotype-specific antibodies conjugated to alkaline phosphatase (for IgM, Sigma; for $IgG_1$, Caltag; for $IgG_3$, Southern Biotechnology Associates). $OD_{405}$ values were obtained using a microplate reader (Molecular Devices).

Results

ST6Gal alleles were mutagenized in embryonic stem cells by homologous recombination and Cre recombinase action (A and B). To achieve a systematic mutation, exon 2 was chosen for deletion. This exon contains the N-terminal 200 amino acids and over 50% of the ST6Gal coding sequence. Deletion of exon 2 results in loss of cytoplasmic, transmembrane, and considerable catalytic domain sequences, such that any resulting stably translated, truncated, and active enzyme would be incapable of entry into the lumen of the endoplasmic reticulum and Golgi apparatus. Mice homozygous for the deleted $ST6Gal^\Delta$ allele were born at normal frequency, were fertile, and did not exhibit abnormalities in weight or overt behavior (B and data not shown). Histologic studies of various tissues including liver, brain, kidney, spleen, and thymus were unremarkable. Additionally, a normal hematologic profile involving leukocytes, erythrocytes, and platelets was observed among peripheral blood samples. Enzymatic studies of liver and splenocyte extracts using the Galβ1-4GlcNAc-octyl acceptor (see Materials and Methods) revealed that mice homozygous for the $ST6Gal^\Delta$ allele were deficient in ST6Gal activity (Table 3), indicating that the exon 2 deletion produced a null mutation.

TABLE 3

ST6Gal activity levels in membranes derived from wild-type (wt/wt) and homozygous-mutant (Δ/Δ) ST6Gal genotypes.

| Genotype | ST6Gal Activity, pmol/min per mg of protein | |
|---|---|---|
| | Liver | Splenocytes |
| wt/wt | 13.4 ± 1.0 | 33.1 ± 9.5 |
| Δ/Δ | 0.3 ± 0.1 | 0.3 ± 0.2 |

Expression of the ST6Gal product was assessed using the *Sambucus nigra*-derived lectin SNA and a recombinant soluble CD 11-Ig lectin chimera, which both bind the Sia6LacNAc trisaccharide with high specificity (Powell et al. (1993) *J. Biol. Chem.* 268: 7019-7027; Sgroi et al. (1993) *J. Biol. Chem.* 268: 7011-7018; Powell & Varki (1994) *J. Biol. Chem.* 269: 10628-10636). In contrast to erythroid and myeloid cells analyzed, lymphocytes were found to highly express cell surface Sia6LacNAc (C). Lymphocytes from mice homozygous for the ST6Gal^A mutation were deficient in binding to SNA and CD22-Ig, whereas mice homozygous for the loxP-flanked ST6Gal^F allele expressed normal levels of Sia6LacNAc on their cell surfaces (C and data not shown). Levels of α2-3-linked sialic acids were visualized using the Maackia amurensis-derived lectin MAL II. No significant changes in α2-3-linked sialic acid levels were thereby observed among lymphoid cells isolated from mice homozygous for the ST6Gal^A allele (C). Residual or low-level SNA and CD22-Ig binding may reflect the presence of Siaα2-6GalNAc on O glycans (Hanasaki et al. (1995) *J. Biol. Chem.* 270: 7533-7542), although it also remains possible that additional enzymes exist that product low levels of Sia6LacNAc. Nevertheless, the deletion generated in the ST6Gal locus results in loss of ST6Gal activity and a deficiency in Sia6LacNAc production at the cell surface, consistent with the described biochemical role of ST6Gal and its' inactivation in mice homozygous for the ST6Gal^A allele. This loss in Sia6LacNAc production was readily detected by the SNA and CD22-Ig lectin binding assays.

Sia6LacNAc-deficient mice contained normal numbers of Gr-1$^+$ myeloid, Ter-119$^+$ erythroid, B220$^+$ B lymphoid, and T lymphoid (CD3$^+$, CD4$^+$, CD8$^+$) cells in the thymus, spleen, lymph nodes, and bone marrow. B lymphocyte development in the bone marrow of ST6Gal-deficient mice was unaltered. The percentage of pro-B cells in the ST6Gal-deficient bone marrow (B220$^{lo}$CD43$^+$, Hardy et al. (1991) *J. Exp. Med.* 173: 1213-1225) was normal. Furthermore, the frequency of immature B cells (B220$^{lo}$ IgM$^{int}$, Carsetti et al. (1995) *J. Exp. Med.* 181: 2129-2140) was not affected by ST6Gal inactivation. Similarly, no statistically significant changes were found in the abundance of mature B cells in the marrow (B220$^{hi}$ IgM$^{int}$ and B220$^{hi}$ HSA$^{lo}$, ref Carsetti et al., supra.) or in the previously defined transitional B cell population undergoing maturation and negative selection (B220$^{lo-hi}$ IgM$^{hi}$, Carsetti et al., supra.).

Although B lymphocyte abundance and development appeared unaltered in Sia6LacNAc-deficient mice, their B cells invariably exhibited reductions in cell surface IgM and CD22. Although HSA levels were unaffected, ST6Gal deficiency resulted in peak IgM levels at 65% of controls and CD22 levels 38% of normal. However, no evidence for B lymphocyte activation was found in analyses of cell surface activation markers CD44, B7.2, and major histocompatibility complex class I (I-A$^b$). Additionally, CD40 expression was unaltered with ST6Gal deficiency. Additional analyses of splenic B cells from Sia6LacNAc-deficient mice revealed normal expression of cell surface CD19, CD21, CD23, and CD45RA$^+$ (B220).

Reductions observed in cell surface IgM and CD22 prompted analyses of serum Ig levels to initially assess B cell function in unimmunized mice. Sia6LacNAc-deficient mice exhibit significant decreases in IgM levels to a median value of 37% of normal while statistically unaltered levels of IgA and IgG were observed. Although Sia6LacNAc deficiency does not impede lymphocyte development of trafficking, dysfunctional B lymphocytes might reside in mice homozygous for the ST6Gal^A allele.

B lymphocyte immune activation proceeds by increased tyrosine phosphorylation and Ca$^{2+}$ mobilization leading to gene activation and proliferation as necessary for effective humoral immunity (Campbell & Sefton (1990) *EMBO J.* 9: 2125-21312; Gold et al. (1990) *Nature* 345: 810-813; Plieman et al. (1994) *Immunol. Today* 15: 393-399; Cooke et al. (1994) *J. Exp. Med.* 179: 425-438). B lymphocytes from control and ST6Gal-deficient mice were isolated from the spleen or lymph nodes and activated by crosslinking cell surface IgM, CD40, or by addition of LPS. Proliferation of ST6Gal-deficient B lymphocytes in response to these stimuli was found to be significantly reduced. Interestingly, normal responsiveness was observed when interleukin-4 (IL-4) was present during the stimulation as various and suboptimal concentrations of stimulatory anti-IgM or anti-CD40 antibodies. IL-4 promotes Ig class switching from IgM to IgG and IgE (Paul, W E (1991) *Blood* 77: 1859-1870; Coffman et al. (1993) *Adv. Immunol.* 54: 229-270) and can synergize with suboptimal antigen-receptor activation likely through coactivation of "down-stream" cytosolic and nuclear signal transduction events. Results observed with IL-4 reveal the intrinsic ability of ST6Gal-deficient B lymphocytes to respond normally in some conditions; however, activation of N lymphocytes through the antigen-receptor complex and following CD40 ligation is adversely affected.

The efficacy of early signal transduction events was assessed by measuring Ca$^{2+}$ mobilization and phosphotyrosine accumulation immediately following anti-IgM stimulation. Cytosolic mobilization of Ca$^{2+}$ from intracellular compartments occurs rapidly upon IgM crosslinking by hydrolysis of inositol phospholipids (Plieman et al., supra., Cooke et al., supra.). B lymphocytes from St6Gal null mice failed to mobilized Ca$^{2-}$ as efficiently as controls with a decrease in both the rate of Ca$^{2+}$ mobilization and the amount of Ca$^{2+}$ mobilized. ST6Gal-deficient B lymphocytes were next analyzed for their ability to accumulate phosphotyrosine on cellular proteins in response to anti-IgM stimulation. CD22 is among those proteins phosphorylated on tyrosine following B cell antigen-receptor activation, and this phosphorylation is reported to recruit the SHP tyrosine phosphatase and other effector molecules to the antigen-receptor complex by SH2 binding interactions (Campbell & Klinman (1995) *Eur. J. Biochem.* 25:1573-1579; Law et al. (1996) *J. Exp. Med.* 183: 547-560). Phosphotyrosine accumulation on CD22 was observed following anti-IgM stimulation of ST6Gal-deficient B cells (however, reduced levels of cell surface CD22 necessitate additional quantitative studies on CD22 localization and relative phosphorylation potential. Nevertheless, among total cellular proteins analyzed following anti-IgM stimulation, a reduction in phosphotyrosine accumulation was noted on a protein migrating at approximately 42 kDa, with varied alterations on proteins of approximately 37 kDa.

The potential physiologic relevance of these alterations was addressed by analyzing the ability of ST6Gal-deficient mice to mount an immune response to T-independent and T-dependent antigens as judged by antibody production. Control and St6Gal-deficient mice were immunized with either DNP-Ficoll (T-independent antigen) or DNP conjugated to (KLH) (T-dependent antigen). Anti-DNP antibody titers were measured at various times after immunization. Mice deficient in Sia6LacNAc consistently failed to generate high titers of anti-DNP antibody following immunization with the T-independent antigen DNP-Ficoll. Control mice produced high anti-DNP IgM titers within 7-10 days of immunization, whereas mice lacking a functional ST6Gal allele were deficient in anti-DNP IgM and IgG$_1$ antibodies, and a reduced response was evident involving anti-DNP IgG$_3$ antibody production. In response to immunization with the T-dependent antigen DNP-KLH, ST6Gal-deficient mice were again severely impaired in their ability to generate an anti-DNP IgM antibody. Following a second "boost" immunization with DNP-KLH, Sia6LacNAc-deficient B cells still yielded reduced anti-DNP IgG$_1$ antibody levels and did not generate significant anti-DNP IgG$_3$ antibody. From these studies it is clear that mice deficient in the Sia6LacNAc trisaccharide are impaired in their ability to mount immune responses.

Discussion

Mice deficient in ST6Gal I appeared normal in most respects, but exhibited hallmarks of profound immunosuppression. Notably, serum levels of IgM were significantly reduced, and the mice were markedly deficient in production of antibodies in response to immunization with T-independent and T-dependent antigens. As biochemical correlates of this phenotype, B lymphocytes were hyporesponsive to IgM and CD40 crosslinking. These studies reveal that the ST6Gal-I sialyltransferase and corresponding production of the Sia6LacNAc trisaccharide ligand of CD-22 is essential for normal B cell activation.

The effector role of the ST6Gal sialyltransferase in B lymphocyte activation discloses an additional level of biologic control operating at the immune cell surface through oligosaccharide variation. Production of the Sia6LacNAc trisaccharide does not appear to be necessary for B lymphocyte development but is required for efficacious immune responses. Although B cells from ST6Gal-deficient mice display a significant reduction in CD22 cell surface levels, this is unlikely to account for the immune deficiencies observed because reduced CD22 expression in mice bearing a heterozygous CD22 null allele did not affect B cell immune function (O'Keefe et al. (1996) Science 274: 798-801; Otipoby et al. (1996) Nature 384: 634-637; Sato et al. (1996) Immunity 5:551-562; Nitschke et al. (1997) Curr. Biol. 7: 133-143). Moreover, ST6Gal-deficient mice present a severe and widespread immunodeficiency much unlike that reported for CD22-deficient mice. Our results indicate that the function of ST6Gal encompasses distinct and unique activities in regulating immune responsiveness that may only partially overlap with the function of CD22.

B cell activation and acquisition of an anergic state reduces cell surface IgM levels, and activation is also reported to downregulate CD22 (Pezzutto et al. (1988) J. Immunol. 140: 1791-1795; Dorken et al. (1988) J. Immunol. 136: 4470-4479).Sia6LacNAc-deficient B cells exhibit characteristics that may reflect prior aberrant antigen-receptor signal transduction leading to an anergic phenotype. Reduced IgM levels on ST6Gal-deficient B lymphocytes is similar to the anergic phenotype that develops following naïve B cell stimulation by endogenous antigen production (Goodnow (1996) Proc. Nat'l. Acad. Sci. USA 93: 2264-2271). Nevertheless, Sia6LacNAc-deficient B cells do not exhibit an activated phenotype. Hypothesis as to how Sia6LacNAc may normally function in mature B lymphocytes requires knowledge of Sia6LacNAc expression.

A subset of secreted or cell surface lymphoid glycoproteins carries the Sia6LacNAc ligand of CD22. Some of these have been identified and include IgM, CD45, and CD22 itself (Stamenkovic et al. (1991) Cell 66: 1133-1144; Braesch-Anderson & Stamenkovic (1994) J. Biol. Chem. 269: 11783-11786; Hanasaki et al. (1995) J. Biol. Chem. 270: 7533-7542; Hickman et al. (1972) J. Biol. Chem. 247: 2156-2163; Sato et al. (1993) Biochemistry 32: 12694-12704). Although selective high-affinity binding of CD22 to soluble IgM has been reported (Hanasaki et al., supra.), the stoichiometry of cell surface CD22-IgM interaction is reported to be low both before and after B cell stimulation (Leprince et al. (1993) Proc. Nat'l. Acad. Sci. USA 90: 3236-3240; Hanasaki et al. (1995) J. Biol. Chem. 270: 7543-7550; Peaker et al. (1993) Eur. J. Biochem. 23: 1358-1363). Because conditions employed in the latter type of experiment can dissociate lectin binding, homotypic and heterotypic cell interactions involving antigen receptors of B and T lymphocytes may normally occur by CD22-CD22 or CD22-CC45 Sia6LacNAc-dependent binding. Within B cells, loss of Sia6LacNAc on IgM and CD22 may thereby lead to aberrant antigen-receptor complex assembly at the cell surface. Perhaps Sia6LacNAc plays a role in the structural stabilization of one or more B lymphocyte membrane molecules that participate in antigen-receptor signal transduction. The observed reductions in serum IgM and cell surface CD22 levels could reflect a destabilizing effect of Sia6LacNAc deficiency, including increased clearance of serum glycoproteins.

Altered protein phosphotyrosine accumulation following ST6Gal-deficient B cell activation nevertheless implies the dysfunction of signal transduction events emanating from the B cell antigen-receptor complex. The identification of altered phosphoproteins would further define the mechanisms by which ST6Gal acts in B cell activation. Such uncertainties are common and presently exist regarding the mechanism of CD22 function (Cyster and Goodnow (1977) Immunity 6: 509-517). It is of importance to understand how molecules that collaborate in signal transduction are able to associate with the B cell antigen-receptor complex in a normal membrane milieu without covalent binding interactions.

The position of oligosaccharides such as Sia6LacNAc at the extracellular side of the plasma membrane indicates that such molecules have evolved to function in cell-cell and receptor subunit interactions (Marth, J. D. (1994) Glycoconjugate J. 11: 3-8; Varki & Marth (1995) Semin. Dev. Biol 6: 127-138). Additionally, the functions of glycosyltransferases and glycosidases have been found in some cases to be focused on a particular cell lineage (Chui et al. (1997) Cell 90: 157-167). In these studies, we have observed the preferential accumulation of Sia6LacNAc on lymphoid cell surfaces among hematopoietic cell types. We have further observed what appears to be a cell-type specific role for ST6Gal and Sia6LacNAc in regulating B lymphocyte immune function. No evidence for T cell dysfunction using in vitro anti-CD3 activation methods has been found thus far. Further research in understanding the B lymphoid role of Sia6LacNAc should illuminate the reason for the more severe and widespread immune deficiency is observed in Sia6LacNAc-deficient mice than in studies of CD22-null mice. It is possible that the presence of CD22 in the absence of its ligand may be especially deleterious to B lymphocyte function by inappropriate localization and sequestration of intracellular signalling molecules. Alternatively, a redundancy in CD22 function mediated by other as yet unidentified Sia6LacNAc-binding lectins operating at the B lymphocyte cell surface that also play important roles in lymphocyte adhesion and intracellular signaling. This latter hypothesis reflects the biologic paradigm exemplified by the sialyl-Lewis X oligosaccharide and the E-, L, and P-selectins in the inflammatory response involving leukocyte intravasation (Butcher and Picker, Science, 272:60 (1996); Maly et al., Cell, 86:643 (1996); Frenette et al. (1996) Cell 84: 573-574)). While these possibilities can be tested, the immunodeficient phenotype of mice lacking Sia6LacNAc provides rationale for using Sia6LacNAc-dependent signal transduction in B cell activation and Sia6LacNAc expression to control immune dysfunction.

Example 5

Diagnosis of Immunodeficiency Associated with Loss of Cytotoxic T Cells

This Example demonstrates that one can diagnose a T lymphocyte-mediated immune system disorder by using the lectins PNA, JAC, and MAL II.

Production of ST3Gal I deficient mice was accomplished similarly to production of ST6Gal deficiency in mice as described in Example 4. The essential difference was the location of the mutation (i.e., the ST3Gal I locus and not the ST6Gal locus). Mutation of the ST3Gal I allele involved deletion of an exon that is essential for ST3Gal I enzyme production (see FIG. 8). While any manner of insertional mutagenesis would also produce the same end result (i.e., ST3Gal I deficiency), we chose to mutate the gene by Cre recombination with deletion of exon 2. Placement of loxP sites in genomic context and surrounding exon 2 is shown in FIG. 8A. In FIG. 8B, the modified ST3Gal I allele is depicted as it occurred in embryonic stem cells following homologous recombination. Subsequently, (FIG. 8C) Cre recombination of ES cells heterozygous for the $F^{[tkneo]}$ allele, followed by ganciclovir selection, provided the type 1 and type 2 deletions. ES cells harboring the type 1 deletion were used to produce mice lacking ST3Gal I function.

Mice lacking a wild-type ST3Gal I allele developed normally and appeared grossly unaltered in a pathogen-free environment. However, as a result of ST3Gal I deficiency, these mice had lost the vast majority of their mature $CD8^+$ T cells. These T cells were deficient from peripheral blood and were also greatly decreased in secondary lymphoid organs (see FIG. 8). The remaining $CD8^+T$ cells appeared inviable, as they were highly apoptotic when isolated. There was only a very minor decrease in the $CD4^+$ helper T cell lineage. These results demonstrate that a deficiency of ST3Gal I dramatically decreases cytotoxic T cell abundance and function.

To develop a simple method for diagnosing this type of immunodeficiency, PNA, JAC, and MAL II were tested for ability to detect the presence or absence of an α2,3-sialylated structure created by the ST3Gal I on the surfaces of cells from non-ST3Gal I-deficient mice. PNA and JAC both bound blood from animals deficient in ST3Gal I, but not blood from non-deficient animals. MAL-II, in contrast, bound normal blood, but not blood from animals deficient in ST3Gal I.

Example 6

Use of a Carbohydrate-Specific Antibody to Detect and Monitor Treatment of an Inherited Glycosylation Disorder Leukocyte Adhesion Deficiency II (LAD II) is a disorder of protein glycosylation that leads to leukocytosis, recurrent infections, severe failure to thrive, and mental retardation. It is caused by inefficient mobilization of fucose. The molecular defect is not known, but many proteins are hypofucosylated. Human serum contains several core-fucosylated glycoproteins, but the most prominent is the μ-chain of immunoglobulin IgM, LADII patients are predicted to be deficient in core fucosylation of this and other serum proteins. This Example describes the use of a specific monoclonal antibody (CAB4; Srikrishna et al. (1997) *J. Biol. Chem.* 272: 25743-25752)) against core Fucα1,6GlcNAc to quantify IgM μ-chain core fucosylation to detect and monitor the course of treatment of LAD II.

Materials and Methods
  A. Reagents
  The monoclonal antibody CAB4, which was originally raised against carbohydrate epitopes of *Dictyostelium discoideum* glycoproteins, specifically recognizes fucose residues in α1,6-linkage to the asparagine-bound GlcNAc of N-linked oligosaccharides (Crandall, I. E. and Newell, P. C. (1989) *Development* 107: 87-94). The antibody was prepared from saturating hybridoma cultures and stored frozen. Mouse specific goat anti-mouse IgG peroxidase was obtained from Sigma. ECL Western blot-peroxidase detection reagent kit was from Amersham Life Sciences, UK.

Western Blot Analysis of Core Fucosylation of Serum Proteins

Serum proteins were separated by SDS/PAGE in 10% polyacrylamide gels (15 μg total protein/lane) under reducing conditions and transferred to nitrocellulose membranes. The membranes were blocked overnight with 10% skimmed milk in PBS, washed with PBS containing 0.05% Tween20, and incubated with CAB4 antibody at concentrations of 20 ng/ml for one hour at room temperature. This was followed by reaction with peroxidase conjugated goat anti-mouse IgG (which was preabsorbed with human proteins to prevent cross reactivity with human IgG). Blots were developed using a peroxidase detection kit.

Results

Fucose therapy was attempted on one LADII patient, in hopes that administration of oral fucose to an LADII patient might result in improved fucosylation of multiple proteins, including IgM. The major serum proteins that are core fucosylated are immunoglobulin heavy chains (γ and μ). Few serum glycoproteins are core fucosylated, and the predominant ones are the immunoglobulin heavy chains. μ chains have five N-glycosylation sites each, three of which are known to be occupied by core α1,6 fucosylated complex N-glycans. γ chain on the other hand has one core fucosylated complex N-glycan.

To verify the effects of fucose therapy on core fucosylation of serum proteins, we performed western blot analysis using CAB4 and a specific anti-mouse IgG secondary antibody that does not cross react with human immunoglobulins. CAB4 is a mouse monoclonal antibody that recognizes α1,6 fucose residues in the core of N-linked glycans (Srikrishna et al., supra.). CAB4 antibody was used to monitor fucosylation of IgM ($T_{1/2}$=5 days) on weekly blood samples. A major protein of approximately 72 kDa was detected in the sera of four different normal individuals but not in the pre-therapy sample from a LAD II patient. The migration of this band corresponded to that of purified human IgM (μ chains).

Figure 7:
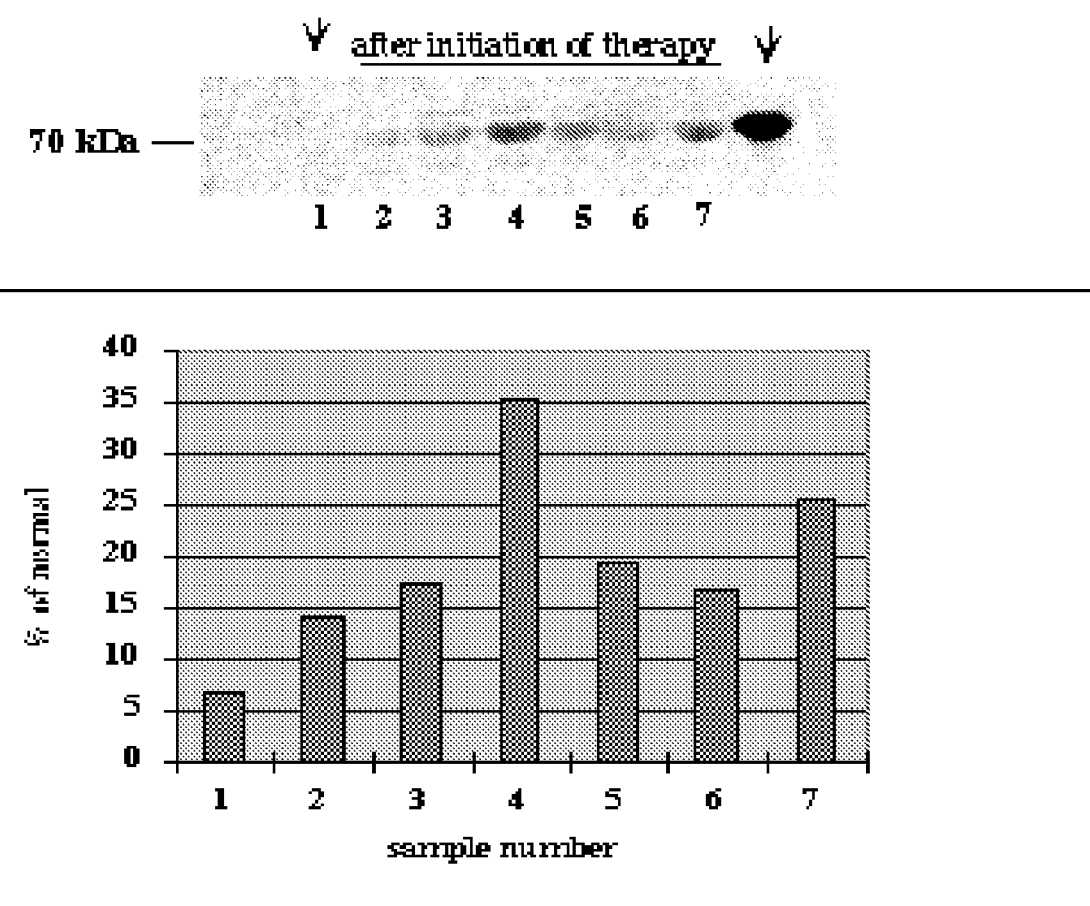
FIG. 7 shows the diagnosis of Leukocyte Adhesion Deficiency II (LAD II) by using the antibody CAB4.

FIG. 7 shows the effect of therapy on core fucosylation of IgM μ chains. Fucosylation was detected within a week of therapy, reaching 35% of normal by four weeks. (The less intense band at 53 kDa corresponds to IgG γ chains). Serum IgM levels on the other hand, showed little variation before and after therapy, suggesting that the increase in core fucosylation is not due a corresponding increase in IgM. There was substantial improvement in IgM core fucosylation compared to before the fucose feeding (<5% normal) Truly remarkable biochemical and clinical improvement was observed in less than two months. Quantitative variations measured with the antibody correlate with measured blood fucose concentrations and inversely with leukocyte counts. Thus, CAB4 can be used to easily measure prognosis of LADII patients on fucose therapy.

In summary, CAB4 was used as a carbohydrate-specific probe in both Western blots and ELISA to monitor the course of fucose therapy. The results of this experiment demonstrated that the LADII patient was severely deficient in core fucosylation compared to a series of healthy controls, and that marked improvement was observed when fucose therapy was employed. Therefore, CAB4 can be used as a simple diagnostic test for patients suspected of having LADII.

We are now developing a dot-blot screening test for LADII based on detection of core fucosylation. The initial results show that a deficiency of 10-20-fold below normal is easily detected.

Example 7

Production of Antibodies for Detecting Underglycosylated Proteins

Antibodies against an unoccupied glycosylation site can be used to detect the presence of underglycosylated proteins such as those found in Carbohydrate Deficient Glycoprotein Syndrome and in active alcoholics. Transferrin is the best documented example of this type of underglycosylation.

Transferrin has two glycosylation sites, one at N432 and another at N630. A synthetic peptide which includes either of these Asn residues in a non-glycosylated state is used to immunize a rabbit or mouse. Since the unoccupied glycosylation site is abnormal, the rabbit or mouse responds by making antibodies that specifically detect the unoccupied glycosylation sequon or a unique conformation of the peptide that results from the absence of glycosylation at that location. One example of a suitable peptide has the amino acid sequence LAENYNKSDNCET (SEQ ID NO:4), which is identical to human transferrin amino acids 427-439. N corresponds to N432, at which site transferrin is normally glycosylated. Another suitable peptide has the amino acid sequence QHLFGSNVTDCSG (SEQ ID NO:5), which is identical to human transferrin amino acids 624-636, with N corresponding to the glycosylation site N630. No other proteins in the data base have this sequence.

Either of these non-glycosylated peptides can be injected directly into a rabbit or mouse or first coupled to a carrier protein such as BSA to produce the desired immune response. The desired antibody will bind to the non-glycosylated peptide, but not to the glycosylated peptide as a criterion of specificity. These antibodies are useful to detect CDGS patients using an ELISA or western blot assay, for example.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

What is claimed is:

1. A method of detecting a genetically transmitted Carbohydrate Deficient Glycoprotein Syndrome (CDGS) in a mammal, the method comprising:
   a) providing a sample from a mammal, wherein the sample comprises a plurality of glycoconjugates;
   b) contacting the sample with at least one of:
      a first type of diagnostic reagent that binds to a first glycoconjugate that has an oligosaccharide determinant that: i) is present on glycoconjugates in a sample obtained from a mammal that has the CDGS, and ii) is absent or is present at reduced levels on glycoconjugates in a sample obtained from a mammal that does not have the CDGS wherein the first type of diagnostic reagent is a lectin; and
      a second type of diagnostic reagent that binds to a second glycoconjugate that has an oligosaccharide determinant that: i) is present on glycoconjugates in a sample obtained from a mammal that does not have the CDGS, and ii) is absent or is present at reduced levels on glycoconjugates in a sample obtained from a mammal that has the CDGS; and
   c) determining whether the diagnostic reagent binds to the glycoconjugates in the sample, wherein the binding of a diagnostic reagent of the first type, or the absence or reduced binding of a diagnostic reagent of the second type, is indicative of the presence of the CDGS in the mammal.

2. The method of claim 1, wherein the sample comprises blood, plasma or serum from the mammal.

3. The method of claim 1, wherein the CDGS is CDGS Type Ia or Type Ib.

4. The method of claim 3, wherein the presence of CDGS Type Ia or Type Ib is detected by the absence or reduced binding of the second type of diagnostic reagent.

5. The method of claim 4, wherein the presence of CDGS Type Ia or Type Ib is detected by the absence or reduced binding of an antibody.

6. The method of claim 4, wherein the presence of CDGS Type Ia or Type Ib is detected by the absence or reduced binding of Con A lectin.

7. The method of claim 4, wherein the presence of CDGS Type Ia or Type Ib is detected by the absence or reduced binding of a lectin.

8. The method of claim 1, wherein the CDGS is CDGS Type II.

9. The method of claim 8, wherein the presence of CDGS Type II is detected by the reduction or absence of binding of at least one of E-PHA lectin and L-PHA lectin to oligosaccharide determinants on the glycoconjugates in the sample.

10. The method of claim 8, wherein the presence of CDGS Type II is detected by the increased binding of Con A lectin to oligosaccharide determinants on the glycoconjugates in the sample.

11. A method of detecting a genetically transmitted Carbohydrate Deficient Glycoprotein Syndrome (CDGS) selected from Type Ia, Type Ib and Type II in a mammal, the method comprising:
   a) providing a sample from a mammal, wherein the sample comprises a plurality of glycoconjugates;
   b) contacting the sample with ConA; and
   c) detecting the ConA bound to the glycoconjugates in the sample, wherein detecting increased binding of ConA is indicative of CDGS Type II and detecting decreased binding of ConA is indicative of CDGS Type Ia or Type Ib in the mammal.

12. A method of detecting a genetically transmitted Carbohydrate Deficient Glycoprotein Syndrome (CDGS) in a mammal, the method comprising:
   a) providing a sample from a mammal, wherein the sample comprises plasma or serum from the mammal;
   b) contacting the sample with at least one of:
      a first type of diagnostic reagent that binds to a first glycoconjugate that has an oligosaccharide determinant that: i) is present on glycoconjugates in a sample obtained from a mammal that has the CDGS, and ii) is absent or is present at reduced levels on glycoconjugates in a sample obtained from a mammal that does not have the CDGS wherein the first type of diagnostic reagent is a lectin or an antibody; and a second type of diagnostic reagent that binds to a second glycoconjugate that has an oligosaccharide determinant that: i) is present on glycoconjugates in a sample obtained from a mammal that does not have the CDGS, and ii) is absent or is present at reduced levels on glycoconjugates in a sample obtained from a mammal that has the CDGS; and c) determining whether the diagnostic reagent binds to the glycoconjugates in the sample, wherein the binding of a diagnostic reagent of the first type, or the absence or reduced binding of a diagnostic reagent of the second type, is indicative of the presence of the CDGS in the mammal.

13. A method of detecting a genetically transmitted Carbohydrate Deficient Glycoprotein Syndrome (CDGS) Type II in a mammal, the method comprising:

a) providing a sample from a mammal, wherein the sample comprises a plurality of glycoconjugates;

b) contacting the sample with at least one of:

a first type of diagnostic reagent that binds to a first glycoconjugate that has an oligosaccharide determinant that: i) is present on glycoconjugates in a sample obtained from a mammal that has the CDGS Type II, and ii) is absent or is present at reduced levels on glycoconjugates in a sample obtained from a mammal that does not have the CDGS Type II wherein the first type of diagnostic reagent is a lectin or an antibody; and a second type of diagnostic reagent that binds to a second glycoconjugate that has an oligosaccharide determinant that: i) is present on glycoconjugates in a sample obtained from a mammal that does not have the CDGS Type II, and ii) is absent or is present at reduced levels on glycoconjugates in a sample obtained from a mammal that has the CDGS Type II; and c) determining whether the diagnostic reagent binds to the glycoconjugates in the sample, wherein the binding of a diagnostic reagent of the first type, or the absence or reduced binding of a diagnostic reagent of the second type, is indicative of the presence of the CDGS Type II in the mammal.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:wild type
      core 2 beta-1,6-N-acetylglucosaminyltransferase (C2
      GlcNAcT) allele PCR primer W5'

<400> SEQUENCE: 1
gggttacgga tgagctctgt gtc                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:wild type
      core 2 beta-1,6-N-acetylglucosaminyltransferase (C2
      GlcNAcT) allele PCR primer W3'

<400> SEQUENCE: 2
ccctggaagc aggacaattc tg                                               22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:mutant core
      2 beta-1,6-N-acetylglucosaminyltransferase (C2
      GlcNAcT) allele PCR loxP primer M3'

<400> SEQUENCE: 3
ctcgaattga tccccgggta c                                                21
```

-continued

```
<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:human
      transferrin amino acids 427-439 synthetic peptide
      including N432 glycosylation site

<400> SEQUENCE: 4

Leu Ala Glu Asn Tyr Asn Lys Ser Asp Asn Cys Glu Thr
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:human
      transferrin amino acids 624-636 synthetic peptide
      including N630 glycosylation site

<400> SEQUENCE: 5

Gln His Leu Phe Gly Ser Asn Val Thr Asp Cys Ser Gly
 1               5                  10
```